(12) United States Patent
Pridgen

(10) Patent No.: US 10,034,846 B2
(45) Date of Patent: *Jul. 31, 2018

(54) FAMCICLOVIR AND CELECOXIB COMBINATION THERAPY FOR FUNCTIONAL SOMATIC SYNDROMES

(71) Applicant: INNOVATIVE MED CONCEPTS, LLC, Tuscaloosa, AL (US)

(72) Inventor: William L. Pridgen, Tuscaloosa, AL (US)

(73) Assignee: INNOVATIVE MED CONCEPTS, LLC, Tuscaloosa, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/597,807

(22) Filed: May 17, 2017

(65) Prior Publication Data

US 2017/0246134 A1 Aug. 31, 2017

Related U.S. Application Data

(63) Continuation of application No. 14/459,905, filed on Aug. 14, 2014, now abandoned, which is a continuation of application No. 13/761,056, filed on Feb. 6, 2013, now Pat. No. 8,809,351.

(60) Provisional application No. 61/595,507, filed on Feb. 6, 2012.

(51) Int. Cl.

| | |
|---|---|
| *A61K 31/196* | (2006.01) |
| *A61K 31/635* | (2006.01) |
| *A61K 31/522* | (2006.01) |
| *A61K 31/52* | (2006.01) |
| *A61K 31/5415* | (2006.01) |
| *A61K 31/415* | (2006.01) |
| *A61K 31/427* | (2006.01) |
| *A61K 31/5575* | (2006.01) |
| *A61K 45/06* | (2006.01) |

(52) U.S. Cl.
CPC .......... *A61K 31/196* (2013.01); *A61K 31/415* (2013.01); *A61K 31/427* (2013.01); *A61K 31/52* (2013.01); *A61K 31/522* (2013.01); *A61K 31/5415* (2013.01); *A61K 31/5575* (2013.01); *A61K 31/635* (2013.01); *A61K 45/06* (2013.01)

(58) Field of Classification Search
CPC .... A61K 31/196; A61K 31/415; A61K 31/52; A61K 31/522; A61K 31/5415; A61K 31/5575; A61K 31/427; A61K 31/635; A61K 45/06

See application file for complete search history.

(56) References Cited

U.S. PATENT DOCUMENTS

| | | |
|---|---|---|
| 4,598,072 A | 7/1986 | Schwelkert et al. |
| 4,658,957 A | 4/1987 | Guth et al. |
| 5,559,114 A | 9/1996 | Exley |
| 8,623,882 B2 | 1/2014 | Pridgen |
| 8,809,351 B2 | 8/2014 | Pridgen |
| 2002/0037501 A1 | 3/2002 | Lerner |
| 2003/0037501 A1 | 2/2003 | Lutrario et al. |
| 2003/0065988 A1 | 4/2003 | Karlquist |
| 2003/0195242 A1 | 10/2003 | Kaufman et al. ............. 514/406 |
| 2003/0211163 A1 | 11/2003 | Chong .......................... 424/489 |
| 2004/0030151 A1 | 2/2004 | Zhuang |
| 2004/0157848 A1 | 2/2004 | Maziasz |
| 2004/0041118 A1 | 3/2004 | Kohlen |
| 2004/0056349 A1 | 3/2004 | Yamada et al. |
| 2004/0072144 A1 | 4/2004 | Lerner |
| 2004/0093870 A1 | 5/2004 | Hara |
| 2004/0208914 A1 | 10/2004 | Richlin et al. ................ 424/448 |
| 2004/0222123 A1 | 11/2004 | Niemann ...................... 206/570 |
| 2004/0229038 A1 | 11/2004 | Cooper et al. |
| 2005/0014729 A1 | 1/2005 | Pulaski ......................... 514/165 |
| 2005/0119194 A1 | 6/2005 | Zeldis et al. |
| 2006/0240037 A1 | 10/2006 | Fey et al. ................. 424/195.15 |
| 2007/0070695 A1 | 3/2007 | Lim et al. |
| 2007/0110685 A1 | 5/2007 | Auspitz et al. |
| 2007/0196457 A1 | 8/2007 | Zhang et al. ................. 424/448 |
| 2007/0280972 A1 | 12/2007 | Zhang et al. ................. 424/400 |
| 2008/0069779 A1 | 3/2008 | Tamarkin et al. .............. 424/45 |
| 2008/0097924 A1 | 4/2008 | Carper et al. |
| 2008/0160007 A1 | 7/2008 | Powell ......................... 424/94.6 |
| 2008/0220079 A1 | 9/2008 | Chen et al. ................... 424/490 |
| 2009/0004281 A1 | 1/2009 | Nghiem et al. ............... 424/490 |

(Continued)

FOREIGN PATENT DOCUMENTS

| | | | |
|---|---|---|---|
| EP | 615750 | 9/1994 | ............. A61K 31/00 |
| EP | 2311446 | 4/2011 | ........... A61K 31/135 |

(Continued)

OTHER PUBLICATIONS

U.S. Appl. No. 13/761,046, filed Feb. 6, 2013, Pridgen.
U.S. Appl. No. 13/761,056, filed Feb. 6, 2013, Pridgen.
U.S. Appl. No. 13/761,059, filed Feb. 6, 2013, Pridgen.
U.S. Appl. No. 13/761,071, filed Feb. 6, 2013, Pridgen.
U.S. Appl. No. 13/761,083, filed Feb. 6, 2013, Pridgen.
U.S. Appl. No. 13/761,088, filed Feb. 6, 2013, Pridgen.
U.S. Appl. No. 13/761,092, filed Feb. 6, 2013, Pridgen.
U.S. Appl. No. 13/761,096, filed Feb. 6, 2013, Pridgen.
U.S. Appl. No. 13/761,079, filed Feb. 6, 2013, Pridgen.
U.S. Appl. No. 14/376,824, filed Aug. 5, 2014, Pridgen.

(Continued)

*Primary Examiner* — Sarah Pihonak
(74) *Attorney, Agent, or Firm* — Harness, Dickey & Pierce, P.L.C.

(57) ABSTRACT

The present invention relates to methods of treating fibromyalgia, by administering a therapeutically-effective combination of an antiviral component and a COX-2 inhibitor component. The invention is further related to pharmaceutical compositions comprising a combination of a therapeutically-effective amount of the antiviral compound famciclovir and a therapeutically-effective amount of the COX-2 inhibitor celecoxib. The invention is also related to methods of treating functional somatic syndromes by administering a therapeutically-effective combination of famciclovir and celecoxib.

15 Claims, 5 Drawing Sheets

(56) References Cited

U.S. PATENT DOCUMENTS

| | | | |
|---|---|---|---|
| 2009/0062315 A1 | 3/2009 | Lee et al. | 514/263.38 |
| 2009/0258947 A1 | 10/2009 | Jain et al. | 514/608 |
| 2010/0129357 A1 | 5/2010 | Garcia-Martinez et al. | 424/133.1 |
| 2010/0136106 A1 | 6/2010 | Liversidge et al. | 424/456 |
| 2010/0222289 A1 | 9/2010 | Lerner | |
| 2011/0105434 A1 | 5/2011 | Exley | |
| 2011/0105611 A1 | 5/2011 | Prados et al. | 514/557 |
| 2011/0112117 A1 | 5/2011 | Exley | 514/263.38 |
| 2011/0217303 A1 | 9/2011 | Smith et al. | 424/135.1 |
| 2011/0275603 A1 | 11/2011 | Muthuppalaniappan et al. | 514/171 |
| 2013/0119710 A1 | 5/2013 | De Luca et al. | |
| 2013/0203710 A1 | 8/2013 | Pridgen | 514/158 |
| 2013/0203742 A1 | 8/2013 | Pridgen | 514/226.5 |
| 2013/0203743 A1 | 8/2013 | Pridgen | 514/226.5 |
| 2013/0203744 A1 | 8/2013 | Pridgen | 514/226.5 |
| 2013/0203780 A1 | 8/2013 | Pridgen | 514/263.4 |
| 2013/0203781 A1 | 8/2013 | Pridgen | 514/263.38 |
| 2013/0203782 A1 | 8/2013 | Pridgen | 514/263.38 |
| 2013/0203783 A1 | 8/2013 | Pridgen | 514/263.38 |
| 2013/0203784 A1 | 8/2013 | Pridgen | 514/263.38 |
| 2014/0221399 A1 | 8/2014 | Pridgen | A61K 31/52 |
| 2014/0357601 A1 | 12/2014 | Pridgen | |
| 2014/0378480 A1 | 12/2014 | Pridgen | |
| 2015/0011538 A1 | 1/2015 | Pridgen | |
| 2015/0011571 A1 | 1/2015 | Pridgen | |

FOREIGN PATENT DOCUMENTS

| | | | |
|---|---|---|---|
| JP | 2006512367 | 4/2006 | A61K 45/06 |
| JP | 2008260728 | 10/2008 | |
| JP | 2009501785 | 1/2009 | A61K 9/2018 |
| JP | 2009521502 | 6/2009 | A61K 9/146 |
| JP | 2011001380 | 1/2011 | A61K 31/436 |
| JP | 2011513433 | 4/2011 | A61K 45/06 |
| WO | WO 1998/52540 | 11/1998 | A61K 9/00 |
| WO | WO 2003/059347 | 7/2003 | A61K 31/415 |
| WO | WO 2003/065988 | 8/2003 | |
| WO | WO 2004/027027 | 4/2004 | A61K 31/436 |
| WO | WO 2004/041118 | 5/2004 | |
| WO | WO 2004/056349 | 7/2004 | A61K 31/00 |
| WO | WO 2007/010559 | 1/2007 | A61K 9/2018 |
| WO | WO 2007/070695 | 6/2007 | A61K 9/12 |
| WO | WO 2007/076415 | 7/2007 | A61K 9/146 |
| WO | WO 2008/097924 | 8/2008 | A61K 31/473 |
| WO | WO 2004/093870 | 11/2008 | A61K 31/34 |
| WO | WO 2009/111739 | 9/2009 | A61K 45/06 |
| WO | WO 2013/119710 | 8/2013 | A01N 43/56 |

OTHER PUBLICATIONS

American Psychiatric Association. (2000) "Anxiety disorders." Diagnostic and Statistical Manual of Mental Disorders DSM-IV-TR. 4th ed., http://www.psychiatryonline.com.

Beck, et al. (1961) "An inventory for measuring depression." Arch Gen Psychiatry, 4:561-571 (With English Translation).

Berg, et al. (1999) "Chronic fatigue syndrome and/or fibromyalgia as a variation of antiphospholipid antibody syndrome: an explanatory model and approach to laboratory diagnosis." Blood Coag Fibrinol., 10:435-438.

J. Bland (2008) "Functional somatic syndromes, stress pathologies, and epigenetics." Alt. Therapies, 14:14-16.

CDC (2012) "Chronic fatigue syndrome: general information." Centers for Disease Control and Prevention, http://www.cdc.gov/cfs/general.

Cephalalgia an International Journal of Headache. (2004) "The international classification of headache disorders." 2nd edition Headache Classification Subcommittee of the International Headache Society, 24(1):1-151.

Clauw, D.J., "Perspectives on Fatigue from the Study of Chronic Fatigue Syndrome and Related Conditions", American Academy of Physical Medicine and Rehabilitation, 2010; 2:414-430.

Clauw, D.J., "Fibromyalgia, A Clinical Review", *American Medical Association*, JAMA, Apr. 16, 2014, vol. 311, No. 15, pp. 1547-1555.

DiFranco, M. et. al. (2010) "Neuroendocrine immunology of fibromyalgia." Ann. N. Y. Acad. Sci., 1193(1):84-90.

FDA (2010) "Guidance for industry codevelopment of two or more unmarketed investigational drugs for use in combination." Draft Guidance (12 pages).

Fantoni, Francesco, Salvetti, Giovanni, Manfredini, Daniele, Bosco, Mario,Stomatologija, "Current concepts on the functional somatic syndromes and temporomandibular disorders", Baltic Dental and Maxillofacial Journal, 2007, vol. 9, No. 1, p. 4.

Fitzgerald, G. et al, "*The Coxibs, Selective inhibitors of Cyclooxygenases-2*", N Engl J Med, vol. 345, No. 6, Aug. 9, 2001, 433-442.

Gebhardt, B. et. al. (2005) "Inhibition of cyclooxygenase 2 synthesis suppresses herpes simplex virus type 1 reactivation." J. Ocul. Pharmacol., 21(2):114-120.

Genlin, et al. (2009) "The effectiveness of repetitive paravertebral injections with local anesthetics and steroids for the prevention of postherpetic neuralgia in patients with acute herpes zoster." Anesthesia & Analgesia, 109(5):1651-1655.

Gesser, R. et. al. (1996) "Oral inoculation with herpes simplex type 1 infects enteric neurons and mucosal nerve fibers within the gastrointestinal tract in mice." J. Virol., 70(6):4097-4102.

Gesser, R. et. al. (1997) "Latent herpes simplex virus type 1 gene expression in ganglia innervating the human gastrointestinal tract." J. Virol., 71(5):4103-4106.

Gur, A. et. al. (2002) "Cytokines and depression in cases with fibromyalgia." J. Rheumatol., 29(2):358-361.

Gur, A. et. al. (2008) "Status of immune mediators in fibromyalgia." Curr. Pain Headache Rep., 12(3):175-181.

Hanno, P. (2002) "Interstitial cystitis epidemiology, diagnostic criteria, clinical markers." Rev. Urol., 4(1):S3-S8.

Hausteiner-Wiehle, C. & Henningsen, P. "Irritable bowel syndrome: Relations with functional, mental and somatoform disorders"; World J Gastroenterol., May 28, 2014; 20(20): 6024-6030.

Henningsen, P. et al. (2007) "Management of functional somatic syndromes." Lancet. 369(9565):946-954.

Hill, J. et. al. (2001) "Gene expression analyzed by microarrays in HSV-1 latent mouse trigeminal ganglion following heat stress." Virus Genes, 23:273-280.

Hurst, H. et al., (2004) "Assessing the clinical significance of change scores recorded on subjective outcome measures." J. Manip. Physiol. Therap. (JMPT), 27(1):26-35.

Kahn, et al. (2010) "Diagnosis and management of IBS." Nature Reviews Gastroenterology and Hepatology, 7:565.

Kanaan, R.A.A., J.P. Lepine & S.C. Wessely, The Association or Otherwise of the Functional Somatic Syndromes: Psychosom Med., Dec. 2007; 69(9): 855-859.

Kelley, K. et. al. (2003) "Cytokine-induced sickness behavior." Brain Behav. Immun., 17:S112-S118.

Kendall, S., et al. (2004) "No effect of antiviral (valacyclovir) treatment in fibromyalgia: a double blind, randomized study." J. Rheumatology, 31(4):783-784.

Leavitt, et al. (2011) "Development of the mental clutter scale." Psychological Reports 109:445-452.

Lerner, A., et al. (2007) "Valacyclovir treatment in epstein-barr virus subset chronic fatigue syndrome: Thirty-six months follow-up." In Vivo, 21(5):707-714.

Ogoina, D. (2011) "Disseminated infections due to immune reconstitution inflammatory syndrome after highly active antiretroviral therapy—report of 3 cases from Nigeria." Pan African Medical Journal, vol. 9(38):1-5.

Payne, January W. (A New Fibromyalgia Remedy: Antiviral Drugs (2008) http://health.usnews.com/health-news/family-health/bones-hoints-and-muscles/articles/2008/04/11/a-new-fibromyalgia-remedy-antiviral-drugs accessed: Mar. 12, 2014).

Pridgen, W.L., et. al. (2007) "Biliary and gastrointestinal manifestations of the herpes simplex virus, type I (HSV-I).", http://tuscaloosasurgery.com/pdf/biliary-gastroherpes-simplex-ibs-final-copy.pdf.

(56) References Cited

OTHER PUBLICATIONS

Quidjada-Carrera, J., et al. (1996), "Comparison of Tenoxicam and Bromazepan in the treatment of fibromyalgia: a randomized, double-blind, placebo-controlled trial", Elsevier Science, 0304-3959/96, pp. 221-225.
Ray, N., et. al. (2004) "Transcriptional response of a common permissive cell type to infection by two diverse alphaherpesviruses." J. Virol., 78(7):3489-3501.
Torpy, D. et. al. (2000) "Responses of the sympathetic nervous system and the hypothalamic-pituitary-adrenal axis to interleukin-6. A pilot study in fibromyalgia." Arthritis Rheum, 43(4):872-880.
Vanderhaeghe, L. (2001) "Stress, aging and cortisol." Total Health, 23:34-35.
Veraldi, et al. (1998) "Verrucous-crusted herpes zoster in an immunocompetent patient." Acta Dermato-Venereologica, 78:236-237.
Wallace, D., et. al. (2006) "Is There a Role for Cytokine Based Therapies in Fibromyalgia." Curr. Pharm. Des., 12(1):17-22.
Wessely S., et al. (1999) "Functional somatic syndromes: one or many?" Lancet, 354:936-939.
Wolfe F., et al. (1990). "The american college of rheumatology 1990 criteria for the classification of fibromyalgia. Report of the multicenter criteria committee." Arthritis Rheum., 33(2):160-172.
Wolfe F., et al. (2010) "The american college of rheumatology preliminary diagnostic criteria for fibromyalgia and measurement of pymptom severity." Arthritis Care & Res. 62(5):600-610.
Notice of Allowance and Fees Due dated Sep. 4, 2013 in U.S. Appl. No. 13/761,083.
Office Action (Restriction Requirement) dated Nov. 7, 2013 issued in U.S. Appl. No. 13/761,096.
Office Action (Restriction Requirement) dated Nov. 15, 2013 issued in U.S. Appl. No. 13/761,092.
Office Action (Restriction Requirement) dated Nov. 29, 2013 in U.S. Appl. No. 13/761,046.
Office Action (Non-Final) dated Aug. 23, 2013 in U.S. Appl. No. 13/761,056.
Office Action (Restriction Requirement) dated Dec. 4, 2013 in U.S. Appl. No. 13/761,071.
Office Action (Final) dated Mar. 18, 2014 in U.S. Appl. No. 13/761,056.
Office Action (Non-Final) dated Apr. 18, 2014 in U.S. Appl. No. 13/761,046.
Office Action (Non-Final) dated Feb. 3, 2014 in U.S. Appl. No. 13/761,071.
Office Action (Non-Final) dated Mar. 21, 2014 in U.S. Appl. No. 13/761,092.
Notice of Allowance and Fees Due dated Jul. 8, 2014 in U.S. Appl. No. 13/761,056.
Office Action (Restriction Requirement) dated Jun. 20, 2014 in U.S. Appl. No. 14/251,345.
Office Action (Advisory Action) dated Jun. 6, 2014 in U.S. Appl. No. 13/761,056.
International Search Report (ISR) and Written Opinion (WO) in PCT/US2013/024991, dated Apr. 10, 2013.
Beaulieu, MD FRCPC, André D., et al., "Once-daily, controlled-release tramadol and sustained—release diclofenac relieve chronic pain due to osteoarthritis: A randomized controlled trial"; *Pain Res Manage* 2008;13(2):103-110.
Quan, MD, Dianna, et al., "Improvement of Postherpetic Neuralgia After Treatment With Intravenous Acyclovir Followed by Oral Valacyclovir FREE", *Arch Neurol.* 2006;63(7):940-942I. Doi:10.1001/archneur.63.7.noc60049. 5 pages.
Staud, Roland; Biology and therapy of fibromyalgia: pain in fibromyalgia syndrome; *Arthritis Research & Therapy*, vol. 8, No. 3; http://artritis-research.com/content/8/3/208, Published: Apr. 24, 2006; 7 pages.
Office Action (Final) dated Aug. 15, 2014 in U.S. Appl. No. 13/761,071.
Office Action (Restriction Requirement) dated Sep. 3, 2014 in U.S. Appl. No. 14/251,345.
Office Action (Non-Final) dated Sep. 8 issued in U.S. Appl. No. 13/761,096.
Dantini, Daniel C., "The New Fibromyalgia Remedy, Stop Your Pain Now with an Antiviral Drug Regimen", Addicus Books, Omaha, 2008, 25 pages.
FDA (2007), "FDA Approves First Drug for Treating Fibromyalgia", 1 page.
Office Action (Ex Parte Quayle) dated Aug. 25, 2014 in U.S. Appl. No. 13/761,092.
Office Action (Restriction Requirement) dated Jun. 25, 2014 in U.S. Appl. No. 13/761,079.
Office Action (Non-Final) dated Oct. 6, 2014 in U.S. Appl. No. 13/761,079.
Office Action (Non-Final) dated Oct. 28, 2014 in U.S. Appl. No. 14/251,345.
Office Action (Non Final) dated Nov. 17, 2014 in U.S. Appl. No. 13/761,046.
Office Action (Restriction Requirement) dated Nov. 21, 2014 in U.S. Appl. No. 14/494,359.
Remington: The science and practice of pharmacy, 2005, Lippincott Williams and Wilkins, 21st edition, p. 1023; pp. 1034-1036 and pp. 1823-1839.
Extended EP Search Report EP151790771 dated Dec. 14, 2015.

FAMCICLOVIR AND CELECOXIB COMBINATION THERAPY FOR FUNCTIONAL SOMATIC SYNDROMES

CROSS-REFERENCE TO RELATED APPLICATIONS

This application is a Continuation Application of U.S. Ser. No. 14/459,905, filed 14 Aug. 2014, which is a Continuation Application of U.S. Ser. No. 13/761,056, filed 6 Feb. 2013, which claims the benefit of U.S. Provisional Application No. 61/595,507, filed on 6 Feb. 2012. The entire disclosures of the above applications are incorporated herein by reference.

FIELD

The present invention relates to pharmaceutical compositions and methods of treating functional somatic syndromes using combination therapies.

BACKGROUND

Fibromyalgia (FM), a common, frequently misdiagnosed systemic disorder that often presents with irritable bowel syndrome (IBS) and chronic fatigue syndrome (CFS), is generally classified as a functional somatic syndrome (FSS). While patients with myalgia, fatigue and other functional somatic complaints have been recognized in the medical literature for centuries, many physicians believe FM and related FSS to be nothing more than a psychosomatic condition. Skeptics have even challenged the validity of FM as a distinct clinical entity, expressing concern about the subjective nature of chronic pain, the lack of standard laboratory tests and the bias of the tender point (TP) examination. Patients with FM typically experience prolonged periods of pain accompanied by stiffness. Associated symptoms may also include sleep disturbances, fatigue, cognitive dysfunction, depressive symptoms, headaches, and anxiety. Patients often report the onset of their symptoms after a period of substantial physical and/or emotional stress.

There is no gold standard for diagnosing FM and there are currently no laboratory tests to diagnose the disorder. Diagnosis is based on symptoms and physical examination. The American College of Rheumatology (ACR) criteria for the classification of FM require the presence of widespread pain for at least 3 months involving 4 quadrants of the body, as well as pressure pain on palpation in at least 11 of 18 standardized anatomical sites. While the etiology and pathogenesis of the disorder are not clearly understood, a combination of interactions among external stressors, behavioral and psychiatric constructs, neurotransmitters, hormones, immune, and sympathetic nervous systems appears to be involved. The initial diagnosis of FM is usually made between the ages of 20 and 50 years. In the United States, an estimated 2% to 4% of the population is affected by FM. Although women comprise 90% of these patients, FM also occurs in men and children of all ethnic groups.

The overabundance of complaints, coupled with the time constraints of a busy medical practice frequently overwhelms physicians, resulting in frustrated physicians and antagonized patients. Unfortunately, the secret to understanding FM may be to evaluate the entire spectrum of complaints. When coupling FM with CFS and IBS, the array of symptoms and signs is daunting to analyze.

The focus of drug therapy for FM is primarily symptomatic. Traditional treatment is multifaceted and includes anti-epileptic medicines such as pregabalin and gabapentin. The U.S. Food and Drug Administration has also approved the serotonin and norepinepherine reuptake inhibitors duloxetine hydrochloride and milnacipran hydrochloride, for management of FM.

Tricyclic antidepressants, selective serotonin reuptake inhibitors, non-steroidal anti-inflammatory analgesics and muscle relaxers have also been used in the management of FM.

The common strategy of choice for most physicians is to decrease pain and to increase function without promoting polypharmacy. Unfortunately, ineffective medical treatment and an excess of prescribed drugs often results in a continued deterioration of the patient's health. Thus there is a need for new, more effective treatments for patients suffering from functional somatic syndromes.

Use of nimesulide, a selective inhibitor of COX-2, is mentioned in U.S. Patent Application Publication No. 2009/0258947, in combination with other active agents, including anti-viral agents, for use in the treatment of NSAID indicated disorders such as fibromyalgia.

Use of selective COX-2 inhibitors (e.g., celecoxib, meloxicam), as mentioned in U.S. Patent Application Publication No. 2003/0195242, can be combined with other compounds known to be effective in reducing but not eliminating the recurrence of herpesviruses (e.g., acyclovir, famcyclovir, viral thymidine kinase inhibitor and other partially effective HSV recurrence inhibitors), for inhibiting the recurrence of a latent herpesvirus infection, such as recurrent ocular herpetic infection which is painful.

Use of valacyclovir, as mentioned by Kendall, et al., in J. Rheumatology (2004) 31, 783-784, for treating fibromyalgia patients, was not successful and valacyclovir was not recommended as therapy for fibromyalgia.

Use of valacyclovir is mentioned by Lerner, et al., in In Vivo (2007) 21, 707-714, for treating chronic fatigue syndrome in a subset of patients with Epstein-Barr virus infection.

Use of a COX-2 inhibitor, as mentioned in U.S. Patent Application Publication No. 2005/0014729, can be combined with one or more dermatologic treatment agents, including antiviral agents (e.g., acyclovir, famciclovir and valacyclovir), for treating dermatological disorders.

Use of acyclovir and diclofenac (as a permitted analgesic) is mentioned by Genlin, et al., in Anesthesia & Analgesia (2009) 109, 1651-1655, for treating postherpetic neuralgia in patients with acute herpes zoster.

Use of selective COX-2 inhibitors, in combination with an anti-herpes virus agent (e.g., acyclovir, famciclovir and valacyclovir), is mentioned in PCT Application Publication No. WO 2004/056349, for treating a herpes virus infection.

Use of a combination of one or more antiviral agents (e.g., acyclovir, famciclovir) and one or more COX-2 inhibitors is mentioned in U.S. Patent Application Publication No. 2003/0211163, for treating papilloma virus infection.

A multiparticulate osmotic delivery system for modified release of at least one drug, as described in U.S. Patent Application Publication No. 2009/0004281, mentions celecoxib, diclofenac, meloxicam and acyclovir, in a listing of drugs that could be used in the delivery system for treating of diseases, including fibromyalgia.

A joint enhancing composition, which can contain a second therapeutic, including diclofenac, celecoxib or acyclovir, is mentioned in U.S. Patent Application Publication No. 2006/0240037, for treating joint disorders, which can include fibromyositis.

A solidifying formulation for dermal delivery of a drug, as mentioned in U.S. Patent Application Publication No. 2007/

0196457, can include acyclovir, famciclovir or valaciclovir for treating herpes viral infections, and diclofenac and COX-2 selective inhibitors for treating pain (e.g., back pain, musculoskeletal pain).

Adhesive solidifying formulations for sustained, dermal drug delivery, described in PCT Application Publication WO 2007/070695, mentions use of acyclovir, famciclovir or valaciclovir for treating herpes viral infections, and diclofenac and COX-2 selective inhibitors for treating pain (e.g., back pain, musculoskeletal pain).

A preparation for topical, transdermal localized delivery of therapeutic agents, as mentioned in U.S. Patent Application Publication No. 2004/0208914, includes diclofenac, celecoxib and meloxicam for treating pain and/or inflammation and antiviral agents, such as acyclovir.

A sustained release pharmaceutical composition, as mentioned in U.S. Patent Application Publication No. 2008/0220079, lists celecoxib, meloxicam and diclofenac as analgesic drugs and acyclovir and valaciclovir as antiviral therapies.

A foamable, vitamin containing composition, as described in U.S. Patent Application Publication No. 2008/0069779, may contain at least one additional therapeutic agent, such as an acyclovir as an antiviral agent, or diclofenac or meloxicam as a non-steroidal anti-inflammatory agent.

A therapeutic, topical formulation, as mentioned in U.S. Patent Application Publication No. 2009/0062315, includes use of an NSAID, such as diclofenac, and an antiviral drug, such as aciclovir, valaciclovir and famciclovir, to treat pain and inflammation caused by herpes virus infection.

A polymeric foam formulation for topical delivery of a therapeutic agent, described in PCT Application Publication WO 2004/041118, mentions use of NSAIDS, such as diclofenac, meloxicam and celecoxib, and antiviral agents, such as acyclovir.

Use of a combination of an antiviral agent (e.g., acyclovir) and an NSAID (e.g., diclofenac), is mentioned in PCT Application Publication WO 1998/52540, for treating symptoms of colds and flu (e.g., sore throat).

Use of antimicrobials, including acyclovir and valacyclovir, in combination with an agent that blocks human dormancy and a third component to reduce adverse effects, such as a COX-2 inhibitor (e.g., CELEBREX®), is mentioned in US Patent Application Publication 2008/0160007, to treat cancer.

Use of dextromethorphan analogs, in combination with anti-infective agents (e.g., acyclovir, valacyclovir) or anti-inflammatory agents (e.g., celecoxib, diclofenac) is mentioned in PCT Application Publication WO 2008/097924, to treat neurological disorders, including fibromyalgia.

Use of valaciclovir and diclofenac is mentioned in Ogoima, D., Pan African Medical Journal (2011) Vol. 9, for treating a patient with disseminated herpes zoster infection.

Use of acyclovir ophthalmic ointment, intravenous acyclovir and oral diclofenac, is mentioned by Veraldi, et al., in Acta Dermato-Venereologica (1998) 78, 236-237, for treating pain and lesions in a patient with verrucuos-crusted herpes zoster infection.

SUMMARY

In one embodiment, there is provided a method for treating a subject susceptible or to or afflicted with fibromyalgia, the method comprising administering to the subject a therapeutically-effective combination of an antiviral component and a COX-2 inhibitor component, wherein the combination administered produces no substantial adverse event.

In another embodiment, there is provided a combination comprising a therapeutically-effective amount of famciclovir and a therapeutically-effective amount of celecoxib.

In another embodiment, there is provided a method for treating a subject susceptible or to or afflicted with one or more functional somatic syndrome conditions comprising: fibromyalgia, chronic fatigue syndrome, irritable bowel syndrome, chronic pain, chronic headache, chronic neck pain, chronic back pain, mood disorder, chronic depression, chronic clinical anxiety disorder, post-traumatic stress disorder (PTSD), brain fog, cognitive dysfunction and chronic interstitial cystitis, the method comprising administering to the subject a therapeutically-effective combination of famciclovir and celecoxib, wherein the combination administered produces no substantial adverse event.

In yet another embodiment, there is kit presentation, comprising a therapeutically-effective amount of famciclovir in a first unit dosage form, and a therapeutically-effective amount of celecoxib, in a second unit dosage form, wherein the first and second unit dosage forms are separately enclosed in one or more containers, arranged in a single package or dispensing device, optionally comprising directions on how to use kit components suitable for administration to obtain a therapeutic outcome.

Further areas of applicability will become apparent from the description provided herein. The description and specific examples in this summary are intended for purposes of illustration only and are not intended to limit the scope of the present disclosure.

DETAILED DESCRIPTION

Figure 1:
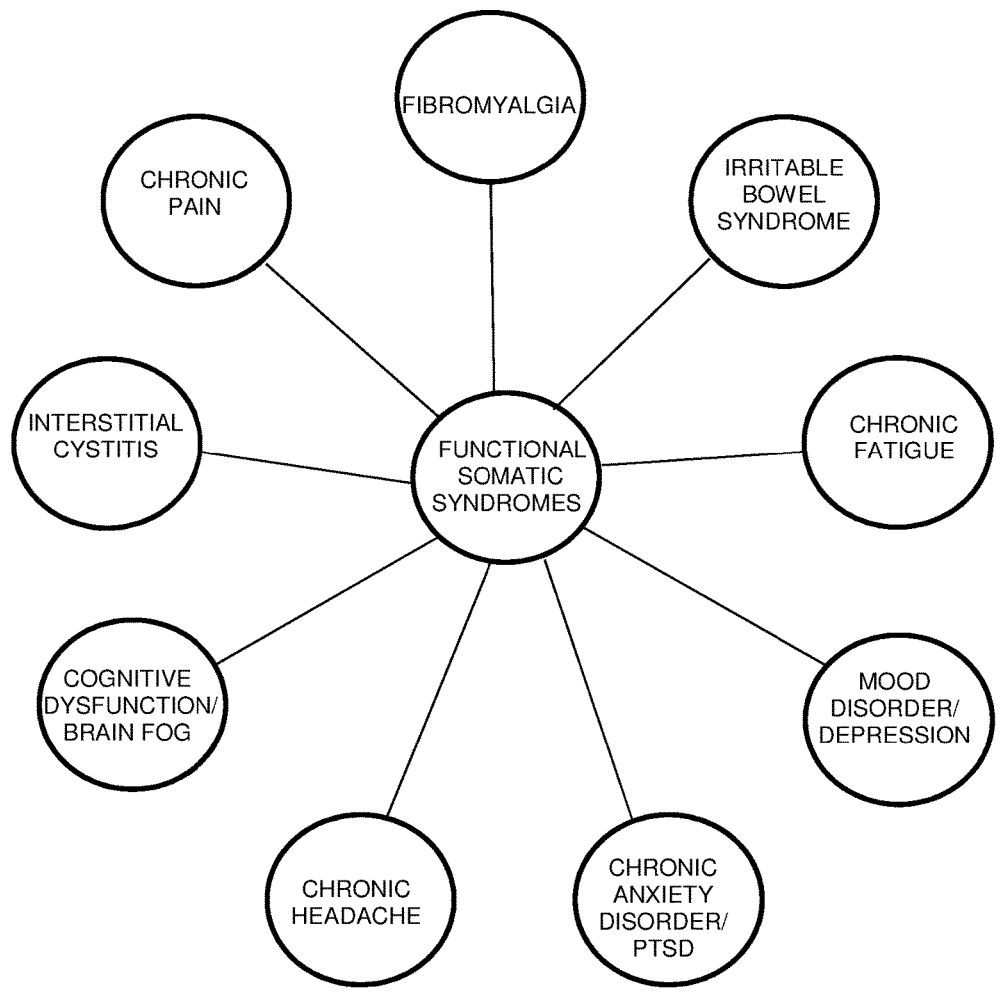
FIG. 1 shows some, but not all, conditions classified as functional somatic syndromes.

The following description is merely exemplary in nature and is not intended to limit the present disclosure, application or uses.

A. Definitions

The term "pharmaceutically acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals, and more particularly in humans.

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "COX-2 inhibitor" refers to a cyclooxygenase-2 inhibitor, which is any pharmaceutically acceptable compound that inhibits the enzyme cyclooxygenase-2.

The term "COX-1 inhibitor" refers to a cyclooxygenase-1 inhibitor, which is any pharmaceutically acceptable compound that inhibits the enzyme cyclooxygenase-1.

The term "HSV-1" refers to herpes simplex virus-1.

The terms "prevent", "prevention", or "preventing" refer to either preventing the onset of preclinically evident condition altogether or preventing the onset of a preclinical evident stage of a condition in a subject. Prevention includes, but is not limited to, prophylactic treatment of a subject at risk of developing a condition.

The term "treat" (and corresponding terms "treatment" and "treating") includes palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to treatment that prevents the occurrence of a condition in a subject. The term "restorative treatment" refers to treatment that halts the progression of, reduces the pathologic manifestations of, or entirely eliminates a condition in a subject.

The term "FM" or "FMS" refer to fibromyalgia and fibromyalgia syndrome, respectively. Fibromyalgia (FM or FMS) is a medical disorder characterized by chronic widespread pain and other symptoms, including but not limited to fatigue, insomnia, depression, allodynia, headaches, irritable bowel syndrome, sensitivity to light, numbness and anxiety symptoms.

The term "CFS" refers to chronic fatigue syndrome. Patients with CFS typically have severe chronic fatigue, not due to ongoing exertion or a medical condition, that significantly interferes with daily activities.

The term "IBS" refers to irritable bowel syndrome. Patients with IBS suffer abdominal pain at least three times a month, not caused by other disease or injury.

The term "cognitive dysfunction", also referred to as "brain fog", "mental fog", or "impaired cognition", refers to the loss or impairment of intellectual function (such as thinking, remembering, or reasoning) of sufficient severity to interfere with daily functioning.

The term "mood disorder" or "depression" refers to a person suffering from a depressed mood or loss of interest or pleasure in daily activities.

The term "chronic anxiety disorder" and "post-traumatic stress disorder" (PTSD) refer to a person suffering from excessive anxiety and worry about a variety of events and situations in a way that is more than would be expected for the particular situation or event.

The term "chronic headache" refers to a person suffering from a headache lasting from 30 minutes to seven days.

The term "interstitial cystitis" refers to a person suffering from pelvic pain and urinary frequency that is of a chronic nature and often unexplained by any known urologic or other system pathology.

The term "chronic pain" refers to a person suffering from persistent, non-acute, sometimes disabling pain in the extremities or other areas of the body, often of unknown origin.

The term "FSS", or "functional somatic syndrome", refers to syndromes typically characterized by multiple physical symptoms, which are not clearly related to demonstrable tissue abnormalities, including, but not limited to, chemical sensitivity, repetition stress injury, chronic whiplash, chronic fatigue syndrome, irritable bowel syndrome, fibromyalgia, chronic pain, chronic headache, chronic neck pain, chronic back pain, chronic depression, chronic clinical anxiety disorder, post-traumatic stress disorder (PTSD), brain fog, cognitive dysfunction and chronic interstitial cystitis.

The term "GERD" refers to gastroesophageal reflux disease.

The term "guanine analog antiviral agent" and "guanine analog antiviral compound" refer to antiviral agents, components or compounds which are synthetic analogs of guanosine which selectively interfere with viral DNA synthesis.

The terms "famcyclovir" and "famciclovir" refer to the same antiviral compound.

The terms "valacyclovir" and "valaciclovir" refer to the same antiviral compound.

The terms "acyclovir" and "aciclovir" refer to the same antiviral compound.

The term "QD" refers to once a day.
The term "BID" refers to two times a day.
The term "TID" refers to three times a day.
The term "QID" refers to four times a day.
The term PO refers to oral administration.

The term "Likert Survey" (and the corresponding term "Likert Scale") refers to a questionnaire which asks subjects the extent to which they agree or disagree with a statement, using a five-point scale.

The term "combination therapy" (or "co-therapy"), in defining use of an antiviral compound and a COX-2 inhibitor, as described herein, is intended to embrace administration of each agent in a sequential manner in a regimen that will provide beneficial effects of the drug combination, and is intended as well to embrace co-administration of these agents in a substantially simultaneous manner, such as by oral ingestion of a single capsule having a fixed ratio of these active agents or ingestion of multiple, separate capsules for each agent. "Combination therapy" will also include simultaneous or sequential administration by intravenous, intramuscular or other parenteral routes into the body, including direct absorption through mucous membrane tissues, as found in the sinus passages. Sequential administration also includes drug combination where the individual elements may be administered at different times and/or by different routes but which act in combination to provide a beneficial effect. It is expected that this combination therapy of an antiviral compound and a COX-2 inhibitor will result in co-action of the antiviral compound and the COX-2 inhibitor, providing a pharmacokinetic interaction, or a pharmacodynamic interaction, or both, where the compounds are administered either simultaneously or sequentially, to permit such co-action.

The term "substantial adverse event", as used, for example, in "no substantial adverse event", refers to one or more unfavorable signs, including one or more abnormal laboratory findings, symptoms or disease conditions associated with the use of a medical treatment or procedure in a subject, that results in a subject's death or risk of dying, hospitalization, permanent damage, disability or impairment of ability to perform one or more daily activities. Examples of impairment of one or more daily activities, as a result of a "substantial adverse event", include being bedridden, unable to perform work at a sedentary job, unable to care for oneself, drive a car or perform housekeeping chores. Causative effects that could produce a substantial adverse event include, for example, headaches, dizziness, palpitations, fainting, vomiting and dehydration.

B. Clinical Observations

The present invention is to be understood as embracing treatment of functional somatic syndromes (FSS), including but not limited to fibromyalgia, as well as pain and associated functional symptoms associated with fibromyalgia. Patients with fibromyalgia were observed to display a variety of symptoms, including but not limited to fatigue, insomnia, depression, allodynia, headaches, irritable bowel syndrome, sensitivity to light, numbness and anxiety. Stress often exacerbates the symptoms. While the etiology and pathogenesis of FSS is not clearly understood, a combination of interactions among external stressors, neurotransmitters, hormones, the immune system, and the sympathetic nervous system, appear to be involved.

Earlier studies, evaluating patients with chronic gastrointestinal disorders (W. L. Pridgen and E. Haggard, "Biliary and Gastrointestinal Manifestations of the Herpes Simplex Virus, Type I (HSV-I)", http://tuscaloosasurgery.com/pdf/biliary-gastroherpes-simplex-ibs-final-copy.pdf), a spectrum of disorders were observed, including functional somatic syndromes such as fibromyalgia, and chronic fatigue syndrome. Based on this experience, it is hypothesized that HSV-1 plays a major role in fibromyalgia and related functional somatic syndromes.

Figure 2:
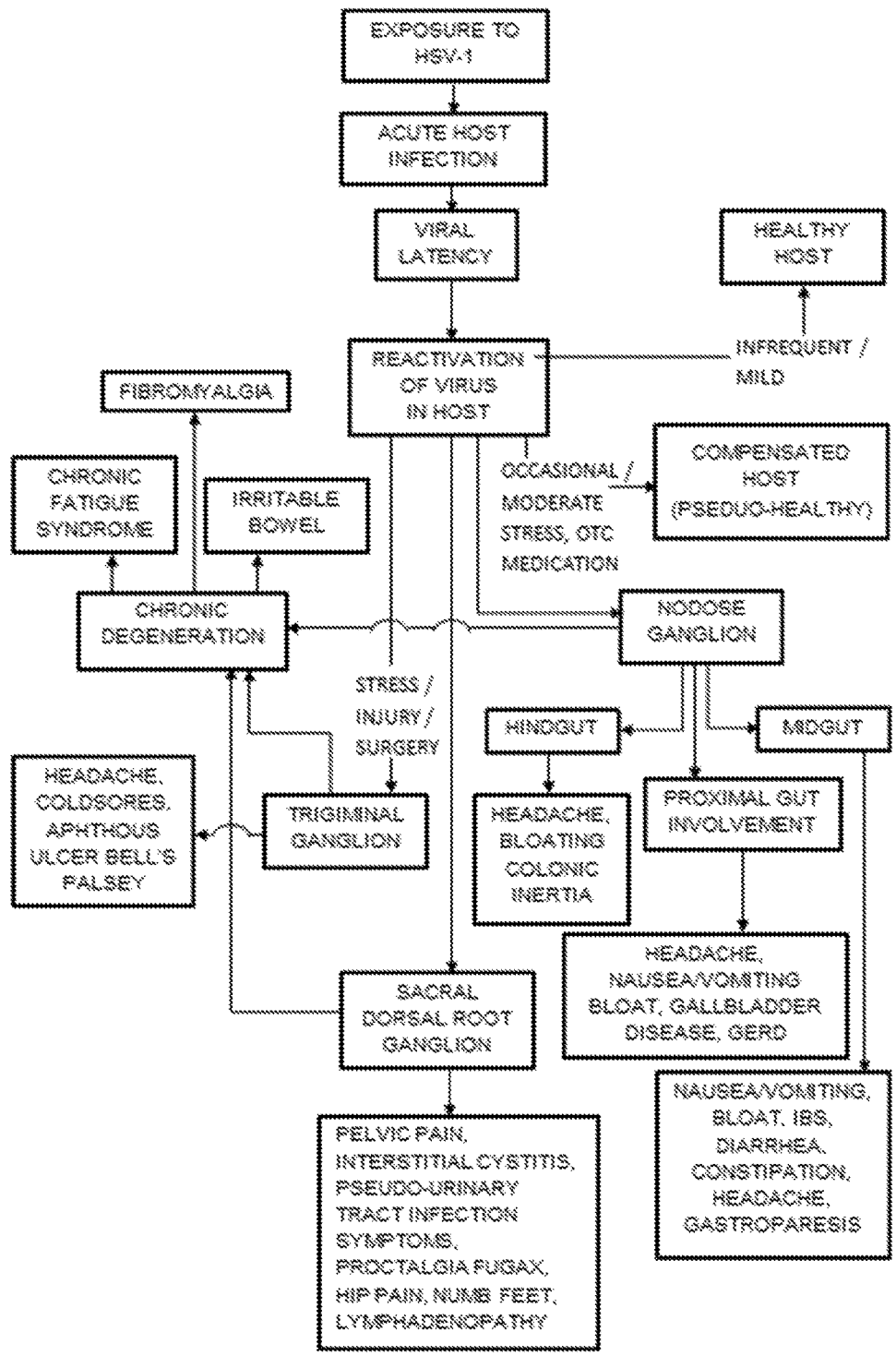
FIG. 2 outlines factual and theoretical relationship of stress, HSV-1, and effects created by involvement of the trigeminal, nodose, and sacral dorsal root ganglia.

The worldwide prevalence rate of HSV-1 is reported to be 98%. The primary target cells are epithelial cells of mucocutaneous membranes. In these cells, HSV-1 replicates efficiently and causes cell lysis. Following the initial replication at the site of entry, the virus gains access to the sensory neurons in the nucleus of the nerve cell bodies where it remains in a state known as latency (see FIG. 2). Primary infection with HSV-1 generally occurs in childhood or early adolescence following inoculation via the eyes, nose, or oral mucosa, or the genital tract. It is less well known that inoculation can also take place through the GI tract. The virus is then transported to the nerve cell nucleus located in the sensory ganglia. Gesser and Koo demonstrated involvement of the ganglion of the vagus nerve (nodose ganglion). They postulated a potential for apoptotic destruction of the ganglion over time [R. Gesser and S. Koo, J. Virol. 70, 4097-4102(1996)], [R. Gesser and S. Koo, J. Virol. 71, 4103-4106(1997)]. Human studies proved the presence of only HSV-1 in the neurons of the mesenteric, submucosal, and periglandular plexuses of the esophagus, stomach, and duodenum. In these studies the spread was specific to the nerve inoculation site rather than that of the circulatory system. The fibers that originated in the nodose ganglion, ultimately terminated centrally in the nucleus tractus solitarius (NTS) [R. Gesser and S. Koo, J. Virol. 71, 4103-4106 (1997)]. Based on the observed development of erosive esophagitis and gastric ulcers in mice, they noted that these ulcers were not directly infected, but were found to overlie virus-infected enteric ganglia. Gesser and Koo postulated that HSV-1 infection of the enteric nervous system is a causal agent in the pathogenesis of chronic recurrent functional human gastrointestinal disorders [R. Gesser and S. Koo, J. Virol. 70, 4097-4102(1996)], [R. Gesser and S. Koo, J. Virol. 71, 4103-4106(1997)].

Herpes viruses are unique because they remain dormant until conditions are sufficient for a reactivation. The stressors in this process may initiate the synthesis and release of peptides and hormones of the sympathetic nervous system and the hypothalamic-pituitary-adrenal axis. Most viruses in this class rarely reactivate. Only two viruses in this family reactivate often enough to create the milieu needed for a chronic debilitating process. We found no evidence for HSV-2 to be the offending organism as it cycles only once or twice a year. Only HSV-1 cycles frequently enough, on average 4 times a year, yet occasionally as often as monthly, to result in the slowly debilitating illnesses. We theorize that after many reactivations, a neuronal cell body dies due to apoptosis and that the ganglion undergoes destruction in the regions governing the first inoculation site.

Figure 3:
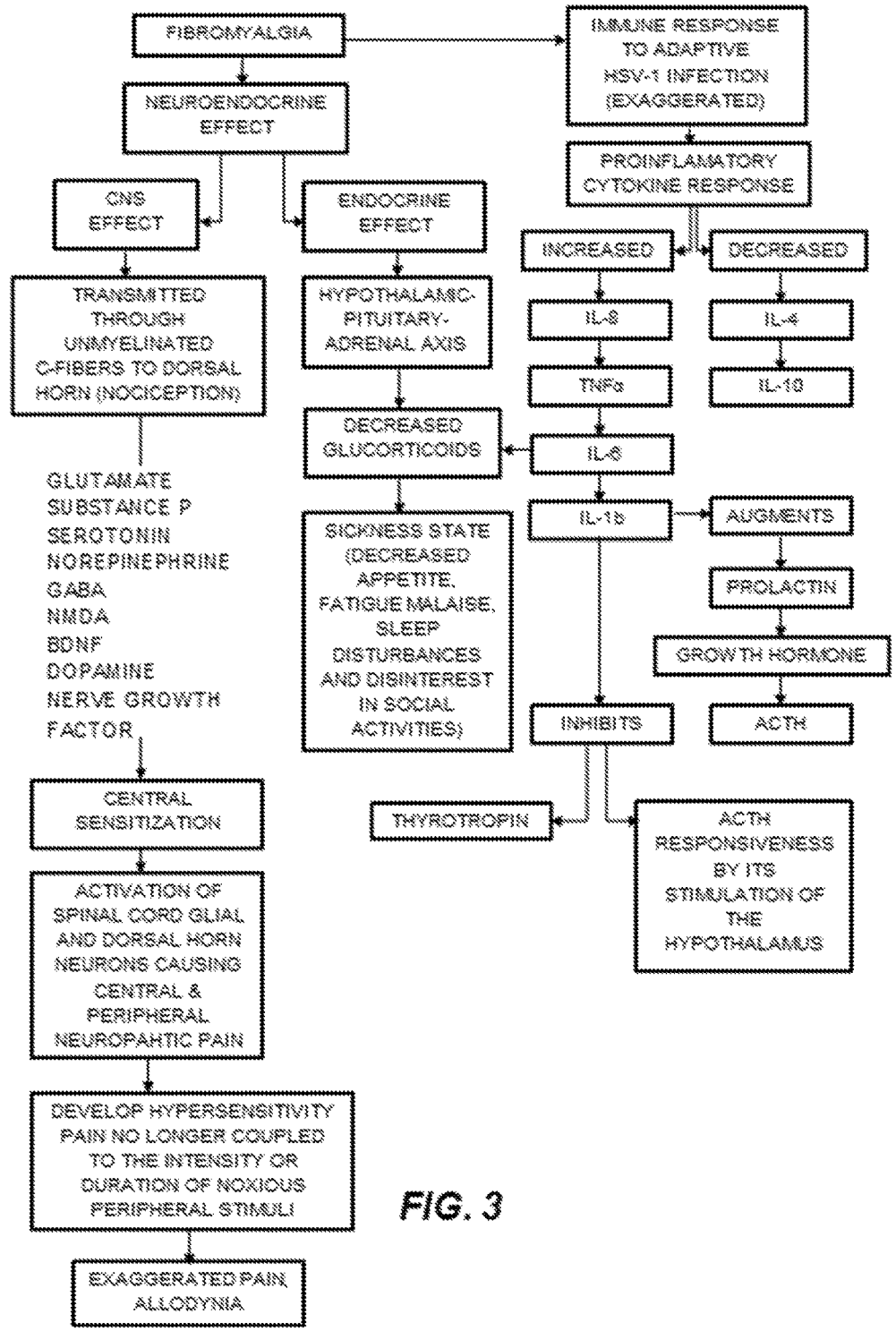
FIG. 3 outlines the effect of fibromyalgia on the nervous, endocrine and immune system, showing HSV-1 as the chronic stressor, and indicates the particular patient symptoms caused by these effects.

The existence of HSV-1 in one or more ganglia may directly or indirectly affect the central nervous system (CNS), hypothalamic pituitary axes (HPA) and immune system (FIG. 3). Dysregulation of pain processing within the CNS may lead to an amplified perception of pain and other sensory stimuli. This phenomenon, often referred to as central sensitization or augmentation, results from changes in the properties of neurons in the CNS where pain is no longer coupled, as acute nociceptive pain is, to the presence, intensity, or duration of noxious peripheral stimuli. Neurotransmitters such as glutamate, Substance P, serotonin, norepinephrine, dopamine, brain-derived neurotrophic factor (BDNF) and gamma aminobutyric acid (GABA), are activated in chronic pain and depression. Substance P, cerebrospinal fluid levels and serum concentration of brain-derived neurotrophic factor have been consistently higher in patients with fibromyalgia compared with controls. Patients with fibromyalgia also have an abnormal dopamine response to pain. Recent data suggest a putative role of pro-inflammatory cytokines, including interleukin-1-beta, tumor necrosis factor-alpha (TNFα), IL-6 and IL-8, in the pathogenesis of fibromyalgia and the modulation of symptoms [M. DiFranco, et al., Ann. N. Y. Acad. Sci. 1193(1), 84-90 (2010)]. Hence pain, as the defining characteristic of fibromyalgia, is not due to tissue damage or inflammation and is thus fundamentally different from rheumatic disorders and many other pain conditions as these conditions cause inflammation in the joints and tissues. HSV-1 has developed various immune evasion mechanisms which prove to be a particular challenge for the immune system. Cytokines and cytokine-induced genes are important for the ability of any organism to raise an antiviral response. Understanding the immune mediators and their possible role in fibromyalgia may be the most daunting obstacles in understanding the disorder. Gur and Oktayoglu [A. Gur and P. Oktayoglu, Curr. Pain Headache Rep. 12(3), 175-181(2008)] explain how cytokines related to acute or repetitive tissue injuries may be responsible for long-term activation of spinal cord glia and dorsal horn neurons, thus resulting in central sensitization. The immune system responds to stressors by causing certain immune cells to secrete the pro-inflammatory cytokines IL-1 and IL-6. Both cytokines are involved in inflammation, and IL-6 is thought to worsen the symptoms of autoimmune disease and fibromyalgia [L. Vanderhaeghe, Total Health 23, 34-35(2001)].

IL-6 and TNFα are increased in autoimmune disorders, osteoporosis, over-exercise, fibromyalgia and osteoarthritis [A. Gur, et al., J. Rheumatol. 29, 358-361(2002)]. The neuroendocrine system (NS) and cytokines also figure in the course of fibromyalgia. The NS responds to stress by activating the HPA-axis. Individuals who have reduced HPA-axis activity often have symptoms of fatigue, depressed mood, myalgias and disturbed sleep. Increased glucocorticoid levels may be related to reduced fatigue and increased wellbeing and energy. Stimulation of the hypothalamus with IL-6 showed delayed adrenocorticotropic hormone (ACTH) responsiveness in fibromyalgia [D. Torpy, et al., Arthritis Rheum. 43, 872-880(2000)]. Cytokines, such as IL-1b, IL-6 and TNFα have been shown to contribute directly to central and peripheral neuropathic pain [D. Wallace, Curr. Pharm. Des. 12, 17-22(2006)].

Fibromyalgia patients often have little motivation to eat, are listless, complain of fatigue and malaise, lose interest in social activities, and have significant changes in sleep patterns. They also are unable to experience pleasure, have exaggerated responses to pain and cannot concentrate. In patients with fibromyalgia, the level of pain intensity can be related to the spinal fluid level of arginine a precursor to nitric oxide [K. Kelley, et al., Brain Behav. Immun. 17, 5112-5118(2003)]. Wallace postulated that activation of glial cells in the brain and spinal cord by substances known to be involved with chronic pain leads to release of IL-1, IL-6, nerve growth factor, NMDA, and Substance P which further perpetuates pain and flu-like symptoms [D. Wallace, Curr. Pharm. Des. 12, 17-22(2006)].

There are lower levels of IL-4 and IL-10 in patients with chronic pain. Chronic pain (dull, aching, or burning) is believed to be transmitted through unmyelinated C fibers to dorsal horn nociceptive neurons. The synapses use glutamate as a neurotransmitter. Nitric oxide promotes the exaggerated release of excitatory amino acids and Substance P from presynaptic afferent terminals and causes the dorsal horn to become hyper-excitable [K. Kelley, et al., Brain Behav. Immun. 17, 5112-5118(2003)].

Figure 4:
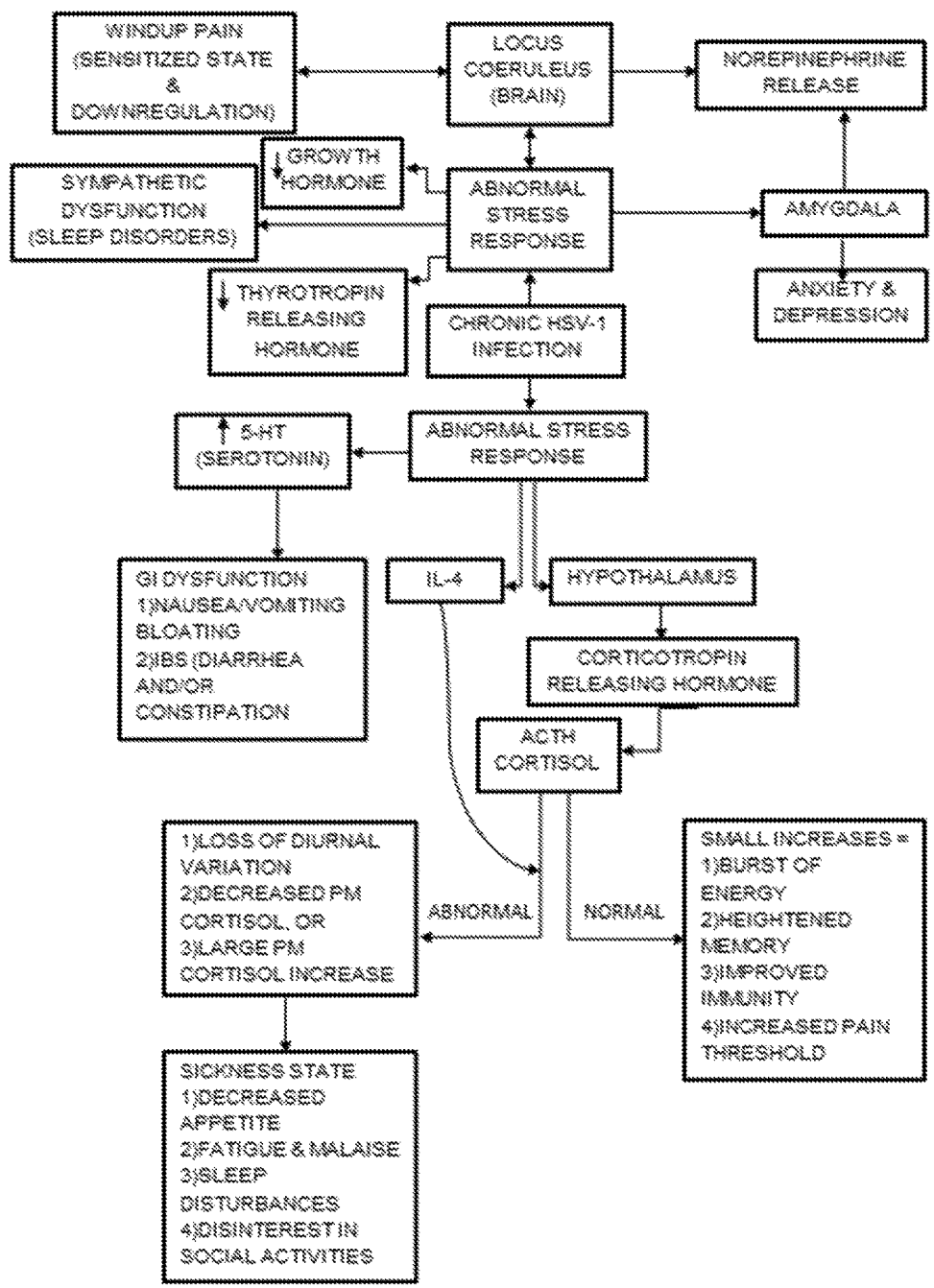
FIG. 4 outlines the abnormal stress response that results in faulty amygdala, locus coeruleus, and hypothalamic-pituitary-adrenal axis function, showing that HSV-1 is the chronic stressor, and indicates the particular patient symptoms caused by these effects.
Figure 5:
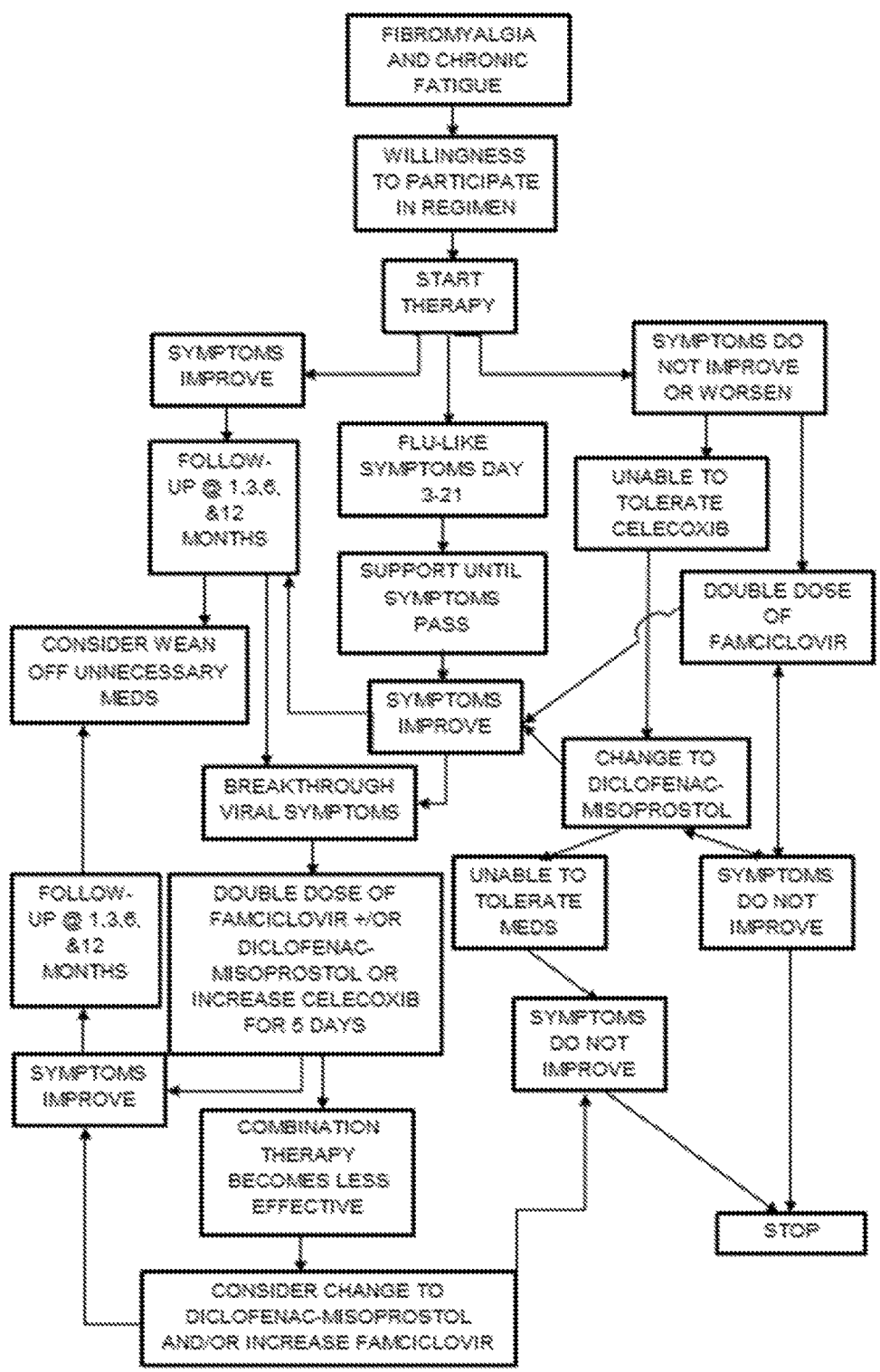
FIG. 5 shows a treatment algorithm for patients suffering from chronic pain, fibromyalgia, chronic fatigue syndrome, other functional somatic syndromes, and other conditions described herein, using a combination of an antiviral compound and a COX-2 inhibitor.

Nociception, neural processing of noxious stimuli, is also thought to play a role in fibromyalgia (FIG. 4). The locus coeruleus is a nucleus in the brain stem involved in mediating sympathetic effects during stress, specifically the synthesis and release of norepinephrine. Fibromyalgia patients are much more sensitive to windup pain, which increases with repetitive stimuli. The locus coeruleus also innervates the amygdala, involved in the emotional processing of pain. This nucleus also innervates the hypothalamus, activating the hypothalamo-pituitary-adrenal axis, stimulating secretion of corticotropin-releasing factor causing release of adrenocorticotropic hormone from the anterior pituitary, increasing cortisol synthesis in the adrenal glands.

Growth hormone deficiency has also been observed in some fibromyalgia patients. Since some symptoms of growth hormone deficiency are similar to those observed in fibromyalgia (e.g., fatigue, depression, muscle weakness, impaired memory) it is believed that growth hormone deficiency may contribute to the pathophysiology of fibromyalgia. Defective growth hormone secretion in fibromyalgia patients may result from increased release of somatostatin by the hypothalamus.

Various studies confirm that isoforms of COX-1 and COX-2 are critical for efficient viral replication. In one study Ray and Enquist showed that simultaneous inhibition of COX-1 and COX-2 caused a dramatic reduction of viral yield after HSV-1 infection [N. Ray and L. Enquist, J. Virol. 78, 3489-3501 (2004)]. Hill, et al., used microarrays to analyze gene expression in the trigeminal ganglion of mice infected with latent HSV-1, and found COX-2 gene expression significantly up regulated after reactivation [J. Hill, et al., Virus Genes 23, 273-280 (2001)]. Gebhardt reported that the selective COX-2 inhibitor celecoxib can suppress hyperthermic stress-induced herpes viral reactivation in the nervous system of mice [B. Gebhardt, et al., J. Ocul. Pharmacol. Ther. 21, 114-120 (2005)].

Functional somatic syndromes (FSS) may be defined as conditions "characterized by patterns of persistent bodily complaints for which adequate examination does not reveal sufficiently explanatory structural or other specified pathology" [P. Henningsen, et al. (2007) Lancet 369, 946-954]. A diverse number of conditions are commonly described as FSS, including: fibromyalgia, irritable bowel syndrome, chronic fatigue syndrome, premenstrual syndrome, non-ulcer dyspepsia, chronic pain, chronic pelvic pain, hypoglycemia, low back pain, sick building syndrome, Gulf War syndrome, tension headache, tempo-mandibular joint disorder, repetitive strain injury, multiple chemical sensitivity, interstitial cystitis, chronic Lyme disease, depression, post-traumatic stress disorder (PTSD), chronic anxiety disorder, food hypersensitivity and brain fog or cognitive dysfunction.

Despite the broad range of FSS conditions, these disease states may have a common etiology, rather than being distinct syndromes. Wessely and colleagues concluded on the basis of a literature review that there was substantial overlap between these conditions and that their similarities were greater than their differences, proposing the concept of a general functional somatic syndrome [S. Wessely, et al. (1999) Lancet 354, 936-939].

A common etiology for FSS was also explored by Bland, who pointed out that when the allostatic load, the combined external and internal stress, exceeds the ability of the patient to maintain allostasis, alterations in function occur giving rise to symptomatic FSS [J. Bland (2008) Alt. Therapies 14, 14-16.]

The rationale for the combination therapy described herein, where it is hypothesized that HSV-1 plays a major causal role in fibromyalgia and other FSS, is based in part on the discovery that the combination of an antiviral compound and a COX-2 inhibitor will increase efficacy in the treatment of these conditions (see Example A).

Additional support for the concept that HSV-1 is a common etiological stressor that gives rise to FSS is provided in the following biopsy studies:

Study Protocol I: HSV-1 DNA and EM Analysis of Human Gastrointestinal Mucosa

Study Purpose:

A number of gastrointestinal (GI) disorders are frequently co-morbid with functional somatic syndromes (FSS) such as but not limited to fibromyalgia and chronic fatigue syndrome. We hypothesize that herpes simplex virus type 1 (HSV-1) plays a major role in the chronic gastrointestinal (GI) disorders associated with FSS. This study uses virus-specific DNA amplification/sequencing, herpesvirus-specific antibodies to demonstrate active infection (immunoblot) and electron microscopy (EM) to demonstrate the presence of the virus in GI biopsies from chronically ill patients who present with both fibromyalgia and an associated GI disorder.

Study Procedure:

In ongoing studies, GI specimens (biopsies) were collected from fibromyalgia patients who are undergoing their routine endoscopic work-up for GI disease. Test samples were obtained from patients that present with both GI disease and fibromyalgia. The specimens were divided, with one part used for medical/diagnostic purposes (sent to pathology) and the other part used for this study.

PCR (polymerase chain reaction) with universal herpesvirus primers were used to amplify any herpesvirus DNA present in the biopsy samples. Herpesvirus DNA was sequenced to determine which herpesvirus was present in the tissue samples. Quantitative PCR using primers specific to the identified herpesvirus was performed to measure and compare the infection levels in test and control samples. Using an antibody specific to a herpesvirus protein produced in infected cells, immunoblot assays were done to determine whether active infection was underway in the biopsied tissue at the time of collection. In subsequent studies, electron microscopy will be performed to reveal the presence of herpesvirus particles in the tissue samples.

The study population includes both men and women ages 19-75 years that suffer from chronic gastrointestinal illnesses. These illnesses include, but are not limited to GERD, irritable bowel syndrome (IBS), colonic inertia, gastroparesis, gastritis, recurrent pancreatitis, and peptic ulcer disease.

Results: 19 fibromyalgia patient tissue biopsies have been tested for the presence of herpesvirus DNA. All but one (18 out of 19 samples) were found to contain herpesvirus DNA. In analyzing the sequences of the herpesvirus DNA found in these 18 samples, all contained only HSV-1 DNA (no other herpesvirus DNA was present). The presence of HSV-1 DNA in the tissue samples is a strong indicator of HSV-1 infection.

It is possible that HSV-1 DNA could be present in a tissue sample without active infection due to the presence of HSV-1 virus particles passing through the GI tract of the patient at the time of biopsy collection. Although this is unlikely to have occurred in all 18 samples that were positive for HSV-1 DNA, a more definitive test was performed for the presence of active HSV-1 infection in the tissue samples collected. In this test, an immunoblot is performed using an antibody specific to a viral protein (ICP8) that is present in virally infected cells, but is not present in free virus particles. Of the 9 positive biopsies examined with immunoblot, 8 were positive for the presence of ICP8, showing active HSV-1 infection was occurring in the GI tracts of these patients at the time of biopsy collection.

| Test performed/Question asked | # of samples tested | # of positive samples |
|---|---|---|
| PCR: Is a herpesvirus present in the tissue? | 19 | 18 |
| DNA sequencing: Is the herpesvirus present in the tissue HSV-1? | 18 | 18 |
| ICP8 immunoblot: Is active HSV-1 infection present in the tissue? | 9 | 8 |

Study Protocol II: Herpesvirus DNA, Protein and Electron Microscopic Analysis of Human Genitourinary Mucosa Study Purpose:

It is hypothesized that herpes simplex virus type 1 (HSV-1) plays a major role in some genitourinary (GU) disorders. This study will use virus-specific detection via DNA amplification/sequencing, immunoblotting, and electron microscopy (EM) to demonstrate the presence of the virus in GU biopsies from chronically ill patients who present with interstitial cystitis.

Study Procedure:

GU specimens (biopsies) will be collected from patients who are undergoing their routine endoscopic work-up. Test samples will be obtained from patients that present with interstitial cystitis disease. Control samples will be obtained from patients that present with GU disorders unrelated to interstitial cystitis. The specimen will be divided, with one part used for medical/diagnostic purposes (sent to pathology) and the other part used for this study.

PCR (polymerase chain reaction) with universal herpesvirus primers will be used to amplify any herpesvirus DNA present in the biopsy samples. Herpesvirus DNA will be sequenced to determine which herpesvirus is present in the tissue samples. Quantitative PCR using primers specific to the identified herpesvirus will be performed to measure and compare the infection levels in test and control samples. Immunoblots using an antibody specific to a herpesvirus protein found in infected cells will be performed to verify active infection. When sample size permits, electron microscopy will be performed to reveal the presence of herpesvirus particles in the tissue samples.

The study sample size is 15 test and 7 control subjects. The study population will include both men and women ages 19-75 years that suffer from interstitial cystitis disease.

Results:

These studies will:
1) determine the presence/absence of herpesvirus DNA in test tissue and control samples,
2) identify the herpesvirus present in test and control samples, and
3) determine if virus numbers are significantly greater in test samples than in control samples.

C. Pharmaceutical Compositions

In one embodiment there is provided a pharmaceutical composition, comprising a pharmaceutically acceptable carrier in combination with a therapeutically-effective amount of an antiviral compound and a therapeutically-effective amount of a COX-2 inhibitor, in a weight ratio range from about one-to-one to about five hundred-to-one of the antiviral compound to the COX-2 inhibitor.

In another embodiment there is provided a pharmaceutical composition, comprising a pharmaceutically acceptable carrier in combination with a therapeutically-effective amount of an antiviral compound and a therapeutically-effective amount of a COX-2 inhibitor, in a weight ratio range from about one-to-one to about one hundred-to-one of the antiviral compound to the COX-2 inhibitor.

In another embodiment there is provided a pharmaceutical composition, comprising a pharmaceutically acceptable carrier in combination with a therapeutically-effective amount of an antiviral compound and a therapeutically-effective amount of a COX-2 inhibitor, in a weight ratio range from about one-to-one to about fifty-to-one of the antiviral compound to the COX-2 inhibitor.

In another embodiment there is provided a pharmaceutical composition, comprising a pharmaceutically acceptable carrier in combination with a therapeutically-effective amount of an antiviral compound and a therapeutically-effective amount of a COX-2 inhibitor, in a weight ratio range from about one-to-one to about twenty-to-one of the antiviral compound to the COX-2 inhibitor.

In another embodiment there is provided a pharmaceutical composition, comprising a pharmaceutically acceptable carrier in combination with a therapeutically-effective amount of an antiviral compound and a therapeutically-effective amount of a COX-2 inhibitor, in a weight ratio range from about one-to-one to about five-to-one of the antiviral compound to the COX-2 inhibitor.

The compounds of the present invention can be administered in a unit dosage from. If desired, multiple doses per day of the unit dosage form can be used to increase the total daily dose.

In another embodiment there is provided a pharmaceutical composition, as described herein, wherein the amount of antiviral compound is present in a unit dosage form from about 250 mg to about 2000 mg.

In another embodiment there is provided a pharmaceutical composition, as described herein, wherein the amount of antiviral compound is present in a unit dosage form from about 250 mg to about 1000 mg.

In another embodiment there is provided a pharmaceutical composition, as described herein, wherein the amount of antiviral compound is present in a unit dosage form from about 250 mg to about 500 mg.

In another embodiment there is provided a pharmaceutical composition, as described herein, wherein the antiviral compound is a guanine analog antiviral compound.

In another embodiment there is provided a pharmaceutical composition, as described herein, wherein the antiviral compound is selected from the group consisting of famciclovir, valacyclovir and acyclovir.

In another embodiment there is provided a pharmaceutical composition, as described herein, wherein the antiviral compound is famciclovir.

In another embodiment there is provided a pharmaceutical composition, as described herein, wherein the amount of famciclovir is present in a unit dosage form from about 250 mg to about 1000 mg.

In another embodiment there is provided a pharmaceutical composition, as described herein, wherein the antiviral compound is valacyclovir.

In another embodiment there is provided a pharmaceutical composition, as described herein, wherein the amount of valacyclovir is present in a unit dosage form from about 1000 mg to about 2000 mg.

In another embodiment there is provided a pharmaceutical composition, as described herein, wherein the antiviral compound is acyclovir.

In another embodiment there is provided a pharmaceutical composition, as described herein, wherein the amount of acyclovir is present in a unit dosage form from about 400 mg to about 1600 mg.

In another embodiment there is provided a pharmaceutical composition, as described herein, wherein the amount of COX-2 inhibitor is present in a unit dosage form from about 7.5 mg to about 600 mg.

In another embodiment there is provided a pharmaceutical composition, as described herein, wherein the amount of COX-2 inhibitor is present in a unit dosage form from about 15 mg to about 300 mg.

In another embodiment there is provided a pharmaceutical composition, as described herein, wherein the amount of COX-2 inhibitor is present in a unit dosage form from about 50 mg to about 200 mg.

In another embodiment there is provided a pharmaceutical composition, as described herein, wherein the COX-2 inhibitor is selected from the group consisting of celecoxib, meloxicam and a diclofenac-misoprostol combination.

In another embodiment there is provided a pharmaceutical composition, as described herein, wherein the COX-2 inhibitor is celecoxib.

In another embodiment there is provided a pharmaceutical composition, as described herein, wherein the amount of celecoxib is present in a unit dosage form from about 50 mg to about 600 mg.

In another embodiment there is provided a pharmaceutical composition, as described herein, wherein the COX-2 inhibitor is meloxicam.

In another embodiment there is provided a pharmaceutical composition, as described herein, wherein the amount of meloxicam is present in a unit dosage form from about 7.5 mg to about 15 mg.

In another embodiment there is provided a pharmaceutical composition, as described herein, wherein the COX-2 inhibitor is a diclofenac-misoprostol combination.

In another embodiment there is provided a pharmaceutical composition, as described herein, wherein the amount of diclofenac is present in a unit dosage form from about 50 mg to about 200 mg and the amount of misoprostol is present in a unit dosage form from about 200 µg to about 800 µg.

In one embodiment there is provided a combination, comprising a therapeutically-effective amount of famciclovir and a therapeutically-effective amount of celecoxib, wherein the amount of famciclovir is present in a unit dosage form from about 125 mg to about 1000 mg, and wherein the amount of celecoxib is present in a unit dosage form from about 100 mg to about 800 mg.

In another embodiment there is provided a combination, as described herein, wherein the amount of famciclovir is present in a unit dosage form from about 125 mg to about 500 mg.

In another embodiment there is provided a combination, as described herein, wherein the amount of famciclovir is present in a unit dosage form from about 500 mg to about 1000 mg.

In another embodiment there is provided a combination, as described herein, wherein the amount of famciclovir is present in a unit dosage form selected from the group consisting of about 125 mg, about 250 mg, about 500 mg and about 1000 mg.

In another embodiment there is provided a combination, as described herein, wherein the amount of famciclovir is present in a unit dosage form of about 250 mg or about 500 mg.

In another embodiment there is provided a combination, as described herein, wherein the amount of celecoxib is present in a unit dosage form from about 100 mg to about 400 mg.

In another embodiment there is provided a combination, as described herein, wherein the amount of celecoxib is present in a unit dosage form from about 400 mg to about 800 mg.

In another embodiment there is provided a combination, as described herein, wherein the amount of celecoxib is present in a unit dosage form selected from the group consisting of about 100 mg, about 200 mg, about 400 mg and about 800 mg.

In another embodiment there is provided a combination, as described herein, wherein the amount of celecoxib is present in a unit dosage form of about 200 mg or about 400 mg.

In another embodiment there is provided a combination, as described herein, wherein the amount of famciclovir is present in a unit dosage form of about 250 mg or about 500 mg, and wherein the amount of celecoxib is present in a unit dosage form of about 200 mg or about 400 mg.

In one embodiment there is provided a kit presentation, comprising a therapeutically-effective amount of famciclovir in a first unit dosage form, and a therapeutically-effective amount of celecoxib, in a second unit dosage form, wherein the first and second unit dosage forms are separately enclosed in one or more containers, arranged in a single package or dispensing device, optionally comprising directions on how to use kit components suitable for administration to obtain a therapeutic outcome.

In another embodiment there is provided a kit presentation, as described herein, wherein the amount of famciclovir is present in a unit dosage form from about 125 mg to about 1000 mg, and wherein the amount of celecoxib is present in a unit dosage form from about 100 mg to about 800 mg.

In another embodiment there is provided a dosage form wherein the amount of drug present may be from about 0.05% to about 95% by weight, more typically from about 2% to about 50% by weight of the dosage form.

For the treatment of the conditions referred to herein, the compounds described herein can be administered as follows:

Oral Administration

The compounds of the present invention may be administered orally, including by swallowing, so that the compound enters the gastrointestinal tract, or absorbed into the blood stream directly from the mouth (e.g., buccal or sublingual administration).

Suitable compositions for oral administration include solid formulations such as tablets, lozenges and capsules, which can contain liquids, gels, or powders.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Tablets may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable lubricants, for use in a tablet, may be present in amounts from about 0.1% to about 5% by weight, and include calcium, zinc or magnesium stearate, sodium stearyl fumarate and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet, may be present in amounts from about 0.1% to about 3% by weight, and include polysorbate 80, sodium dodecyl sulfate, talc and silicon dioxide.

Parenteral Administration

Compounds of the present invention may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present invention may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

Kits

Compound combinations of the present invention, wherein component A is an antiviral compound and component B is a COX-2 inhibitor as described herein, can be provided in a kit presentation, comprising an arrangement of components A and B in association with each other, as in a single package or in a drug dispensing device. Such kit presentations, used by a patient, may be dispensed by a hospital-formulary, retail pharmacist, or prescribing-physician.

In one example, the kit may comprise a single package, with therapeutically-effective doses of components A and B, in the form of tablets or capsules in separate containers (e.g., bottles) held separately, as in a tray, and bound together in a single package using, for example, shrink wrap, tape, or a plastic or cardboard box enclosing the components.

In another example, separate, therapeutically-effective doses of combination components A and B, in the form of tablets or capsules, may be presented as co-packaged, in a single blister pack.

In another example, the kit presentation may provide therapeutically-effective doses of combination components A and B, in the form of tablets or capsules, which are co-dispensed from a device which delivers the components from a storage receptacle using, for example, one or more levers to co-dispense individual dose forms of components A and B to be administered in combination.

The kit presentation may also be used for parenteral administration of dose forms of Components A and B. For example, individual doses of components A and B in the form of lyophilized powders, either separately or with components A and B mixed together in therapeutically-effective doses, arranged in a package also comprising separately contained vials of sterile water or buffer solution, and optionally a sterile packaged syringe for administration of the dose combination following dissolution.

The kit presentation may further comprise directions, in compliance with approved instructions from a government agency (e.g., U.S. FDA), on how to use the kit components suitable for administration to obtain a therapeutic outcome.

D. Methods of Treatment

The present disclosure further provides for treating a condition in a subject having or susceptible to having such a condition, by administering to the subject a therapeutically-effective amount of the compounds as described above. In one embodiment, the treatment is preventative treatment. In another embodiment, the treatment is palliative treatment. In another embodiment, the treatment is restorative treatment.

In one embodiment there is provided a method to treat a subject susceptible to or afflicted with a condition selected from the group consisting of fibromyalgia, chronic fatigue syndrome, irritable bowel syndrome, chronic pain, chronic headache, chronic neck pain, chronic back pain, chronic depression, chronic clinical anxiety disorder, post-traumatic stress disorder (PTSD), brain fog, cognitive dysfunction and chronic interstitial cystitis, the method comprising administering to the subject a therapeutically-effective amount of an antiviral compound and a therapeutically-effective amount of a COX-2 inhibitor, in a dose weight ratio range from about one-to-one to about five hundred-to-one of the antiviral compound to the COX-2 inhibitor.

In another embodiment there is provided a method, as described herein, wherein the dose weight ratio range is from about one-to-one to about one hundred-to-one of the antiviral compound to the COX-2 inhibitor.

In another embodiment there is provided a method, as described herein, wherein the dose weight ratio range is from about one-to-one to about fifty-to-one of the antiviral compound to the COX-2 inhibitor.

In another embodiment there is provided a method, as described herein, wherein the dose weight ratio range is from about one-to-one to about twenty-to-one of the antiviral compound to the COX-2 inhibitor.

In another embodiment there is provided a method, as described herein, wherein the dose weight ratio range is from about one-to-one to about five-to-one of the antiviral compound to the COX-2 inhibitor.

In another embodiment there is provided a method, as described herein, wherein the condition is a combination of fibromyalgia, chronic fatigue syndrome and irritable bowel syndrome, coexistent in the subject.

In another embodiment there is provided a method, as described herein, wherein the amount of antiviral compound is present in a unit dosage form from about 250 mg to about 2000 mg.

In another embodiment there is provided a method, as described herein, wherein the amount of antiviral compound is present in a unit dosage form from about 250 mg to about 1000 mg.

In another embodiment there is provided a method, as described herein, wherein the amount of antiviral compound is present in a unit dosage form from about 250 mg to about 500 mg.

In another embodiment there is provided a method, as described herein, wherein the antiviral compound is a guanine analog antiviral compound.

In another embodiment there is provided a method, as described herein, wherein the antiviral compound is selected from the group consisting of famciclovir, valacyclovir and acyclovir.

In another embodiment there is provided a method, as described herein, wherein the antiviral compound is famciclovir.

In another embodiment there is provided a method, as described herein, wherein the amount of famciclovir is present in a unit dosage form from about 250 mg to about 1000 mg.

In another embodiment there is provided a method, as described herein, wherein the antiviral compound is valacyclovir.

In another embodiment there is provided a method, as described herein, wherein the amount of valacyclovir is present in a unit dosage form from about 1000 mg to about 2000 mg.

In another embodiment there is provided a method, as described herein, wherein the antiviral compound is acyclovir.

In another embodiment there is provided a method, as described herein, wherein the amount of valacyclovir is present in a unit dosage form from about 400 mg to about 1600 mg.

In another embodiment there is provided a method, as described herein, wherein the amount of COX-2 inhibitor is present in a unit dosage form from about 7.5 mg to about 600 mg.

In another embodiment there is provided a method, as described herein, wherein the amount of COX-2 inhibitor is present in a unit dosage form from about 15 mg to about 300 mg.

In another embodiment there is provided a method, as described herein, wherein the amount of COX-2 inhibitor is present in a unit dosage form from about 50 mg to about 200 mg.

In another embodiment there is provided a method, as described herein, wherein the COX-2 inhibitor is selected from the group consisting of celecoxib, meloxicam and a diclofenac-misoprostol combination.

In another embodiment there is provided a method, as described herein, wherein the COX-2 inhibitor is celecoxib.

In another embodiment there is provided a method, as described herein, wherein the amount of celecoxib is present in a unit dosage form from about 50 mg to about 600 mg.

In another embodiment there is provided a method, as described herein, wherein the COX-2 inhibitor is meloxicam.

In another embodiment there is provided a method, as described herein, wherein the amount of meloxicam is present in a unit dosage form from about 7.5 mg to about 15 mg.

In another embodiment there is provided a method, as described herein, wherein the COX-2 inhibitor is a diclofenac-misoprostol combination.

In another embodiment there is provided a method, as described herein, wherein the amount of diclofenac is present in a unit dosage form from about 50 mg to about 200 mg and the amount of misoprostol is present in a unit dosage form from about 200 µg to about 800 µg.

In another embodiment there is provided a method, as described herein, wherein the method further comprises increasing the daily dose of the antiviral compound to 1.5 to 3 times the daily dose, for a period of not more than five days following onset of an episode of increased symptoms related to fibromyalgia, chronic fatigue syndrome or irritable bowel syndrome.

In another embodiment there is provided a method, as described herein, wherein the method further comprises increasing the daily dose of the COX-2 inhibitor to 1.5 to 3 times the daily dose, for a period of not more than five days following onset of an episode of increased symptoms related to fibromyalgia, chronic fatigue syndrome or irritable bowel syndrome.

In another embodiment there is provided a method, as described herein, wherein the method results in a reduction in the administration of at least one additional therapeutic compound previously administered to the subject.

In another embodiment there is provided a method, as described herein, wherein the method results in a reduction in the administration of at least one additional therapeutic compound previously administered to the subject selected from the group consisting of gabapentin, clonazepam, pregabalin, duloxetine, milnacipran, amitriptyline, fluoxetine, tramadol, morphine, sleep aids and muscle relaxers.

In another embodiment there is provided a method, as described herein, wherein the subject is susceptible to or infected with an HSV-1 virus, wherein the HSV-1 virus infection causes a condition selected from the group consisting of fibromyalgia, chronic fatigue syndrome, irritable bowel syndrome, chronic pain, chronic headache, chronic neck pain, chronic back pain, chronic depression, chronic clinical anxiety disorder, post-traumatic stress disorder (PTSD), brain fog, cognitive dysfunction and chronic interstitial cystitis, the method comprising administering to the subject a therapeutically-effective amount of an antiviral compound and a therapeutically-effective amount of a COX-2 inhibitor, in a dose weight ratio range from about one-to-one to about five hundred-to-one of the antiviral compound to the COX-2 inhibitor.

In another embodiment there is provided a method, as described herein, wherein the combination therapy is administered chronically or continuously over long periods of time (months to years). Chronic therapy with antiviral compounds alone is usually avoided because it can increase the incidence of adverse effects. In addition, prolonged treatment with antiviral compounds alone can induce the emergence of drug-resistant viral strains.

Drug resistance occurs when a disease no longer responds to a therapeutic treatment. For example, drug resistance can result from mutation of a gene, targeted by the antiviral drug, which is necessary for viral replication. The efficacy of an antiviral drug can be prolonged or restored by administering the antiviral compound in combination with a second component, such as a COX-2 inhibitor, as described herein. The second component can induce additional, simultaneous stress on the virus, thus increasing the efficacy of the therapeutic combination.

In one embodiment there is provided a method to treat a subject susceptible to or afflicted with fibromyalgia, the method comprising administering to the subject a therapeutically-effective combination of an antiviral component and a COX-2 inhibitor component, wherein the amount of the antiviral component is administered in a total daily dose range from about 250 mg to about 2000 mg, and wherein the amount of the COX-2 inhibitor component is administered in a total daily dose range from about 15 mg to about 800 mg, and wherein the combination administered produces no substantial adverse event.

In another embodiment there is provided a method, as described herein, wherein the antiviral component is administered in a total daily dose range from about 250 mg to about 1000 mg.

In another embodiment there is provided a method, as described herein, wherein the antiviral component is administered in a total daily dose range from about 500 mg to about 2000 mg.

In another embodiment there is provided a method, as described herein, wherein the antiviral component is administered in a total daily dose range from about 400 mg to about 1600 mg.

In another embodiment there is provided a method, as described herein, wherein the COX-2 inhibitor component is administered in a total daily dose range from about 200 mg to about 800 mg.

In another embodiment there is provided a method, as described herein, wherein the COX-2 inhibitor component is administered in a total daily dose range from about 15 mg to about 30 mg.

In another embodiment there is provided a method, as described herein, wherein the COX-2 inhibitor component is administered in a total daily dose range from about 100 mg to about 150 mg.

In another embodiment there is provided a method, as described herein, wherein the antiviral component is administered in a daily dose of about 500 mg, and wherein the COX-2 inhibitor component is administered in a daily dose of about 400 mg.

In one embodiment there is provided a method to treat a subject susceptible to or afflicted with one or more functional somatic syndrome conditions comprising: fibromyalgia, chronic fatigue syndrome, irritable bowel syndrome, chronic pain, chronic headache, chronic neck pain, chronic back pain, chronic depression, chronic clinical anxiety disorder, post-traumatic stress disorder (PTSD), brain fog, cognitive dysfunction and chronic interstitial cystitis, the method comprising administering to the subject a therapeutically-effective combination of famciclovir and celecoxib, wherein the amount of famciclovir is administered in a total daily dose range from about 250 mg to about 1000 mg, and wherein the amount of celecoxib is administered in a total daily dose range from about 200 mg to about 800 mg, and wherein the combination administered produces no substantial adverse event.

In another embodiment there is provided a method, as described herein, wherein the condition is selected from the group consisting of fibromyalgia, chronic fatigue syndrome, irritable bowel syndrome, chronic depression, chronic clinical anxiety disorder and chronic interstitial cystitis.

In another embodiment there is provided a method, as described herein, wherein the condition is fibromyalgia.

In another embodiment there is provided a method, as described herein, wherein the condition is chronic fatigue syndrome.

In another embodiment there is provided a method, as described herein, wherein the condition is irritable bowel syndrome.

In another embodiment there is provided a method, as described herein, wherein the condition is a combination of fibromyalgia, chronic fatigue syndrome and irritable bowel syndrome, coexistent in the subject.

In another embodiment there is provided a method, as described herein, wherein the amount of famciclovir is administered in a total daily dose range from about 250 mg to about 750 mg, and wherein the amount of celecoxib is administered in a total daily dose range from about 200 mg to about 500 mg.

In another embodiment there is provided a method, as described herein, wherein the amount of famciclovir administered in a total daily dose is about 500 mg, and wherein the amount of celecoxib administered in a total daily dose is about 400 mg.

E. Subjects

Suitable subjects to be treated according to the present invention include mammalian subjects. Mammals according to the present invention include, but are not limited to, human, canine, feline, bovine, caprine, equine, ovine, porcine, rodents, lagomorphs, primates, and the like, and encompass mammals in utero. Subjects may be of either gender and at any stage of development.

F. Combinations and Combination Therapy

The compounds of the present invention, an antiviral compound and a COX-2 inhibitor, can be used as described herein or in combination with other pharmaceutically active compounds, to treat conditions such as those previously described above. The compounds of the present invention, an antiviral compound and a COX-2 inhibitor, and other pharmaceutically active compound(s) can be administered simultaneously (either in the same dosage form or in separate dosage forms) or sequentially. Accordingly, in one embodiment, the present invention comprises methods for treating a condition by administering to the subject therapeutically-effective amounts of the compounds of the present invention, an antiviral compound and a COX-2 inhibitor, and one or more additional pharmaceutically active compounds.

In another embodiment, there is provided a pharmaceutical composition comprising the compounds of the present invention, an antiviral compound and a COX-2 inhibitor, one or more additional pharmaceutically active compounds, and a pharmaceutically acceptable carrier.

In another embodiment, the one or more additional pharmaceutically active compounds are administered in any order or even simultaneously with the compounds of the present invention, an antiviral compound and a COX-2 inhibitor. If simultaneously, the multiple therapeutic agents are optionally provided in a single, unified form, or in multiple forms (by way of example only, either as a single pill or as two or more separate pills).

EXAMPLES

The following example are merely illustrative, and do not limit this disclosure in any way.

Example A

Human Clinical Trials

Objective:
To explore the efficacy of the combination of celecoxib+famciclovir in the treatment of patients diagnosed with one or more functional somatic syndromes.

Study Design:
During the first week of treatment, a loading dose of 500 mg famciclovir twice a day (BID) was employed, followed by a maintenance dose of 250 mg famciclovir BID. The celecoxib dosage, 200 mg BID, remained constant throughout treatment.

Patient Population and Diagnostic Criteria:
Patients selected were adult men and women, with a documented diagnosis of one or more functional somatic syndromes. Screening assessment included a medical and psychological history and physical examination.

Nine distinct but related, and often-overlapping, conditions were treated by the combination therapy described herein. The nine conditions are:
1. Fibromyalgia
2. Irritable bowel syndrome
3. Chronic fatigue
4. Mood disorder/depression
5. Chronic anxiety disorder/PTSD
6. Chronic headache
7. Impaired cognition/brain fog
8. Interstitial cystitis
9. Chronic pain Clinically, there is often observed overlap of each of these conditions with one another in the typical patient. For example one rarely sees a patient with fibromyalgia without elements of chronic fatigue syndrome, chronic headaches, and mood disorders. Below are disease descriptions and criteria used to diagnose these conditions:

1. Fibromyalgia-1990 ACR Diagnostic Criteria:

Pain on both sides of the body, above and below the waist In addition, axial skeletal pain (cervical spine, anterior chest, thoracic spine or low back pain) must be present. Pain in 11 of 18 tender point sites on digital palpation Digital palpation should be performed with an approximate force of 4 kg.
(Wolfe F. Smythe H A. et al. (1990) Arthritis Rheum. 33, 160-172)

2. Irritable Bowel Syndrome

IBS is diagnosed when a person has abdominal pain or discomfort at least three times per month for the last 3 months without other disease or injury that could explain the pain. The pain or discomfort of IBS may occur with a change in stool frequency or consistency or may be relieved by a bowel movement.

To meet the definition of IBS, the pain or discomfort should be associated with two of the following three symptoms:
   i) Start with bowel movements that occur more or less often than usual
   ii) Start with stool that appears looser and more watery or harder and more lumpy than usual
   iii) Improve with a bowel movement
(Kahn, et al. (2010) Nature Reviews Gastroenterology and Hepatology 7:565)

3. Chronic Fatigue Syndrome

Center for Disease Control Criteria for CFS diagnosis requires three criteria:
   i) The individual has had severe chronic fatigue for 6 or more consecutive months that is not due to ongoing exertion or other medical conditions associated with fatigue
   ii) The fatigue significantly interferes with daily activities and work
   iii) The individual concurrently has 4 or more of the following 8 symptoms:
      (a) post-exertion malaise lasting more than 24 hours
      (b) unrefreshing sleep
      (c) significant impairment of short-term memory or concentration
      (d) muscle pain
      (e) pain in the joints without swelling or redness
      (f) headaches of a new type, pattern, or severity
      (g) tender lymph nodes in the neck or armpit
      (h) a sore throat that is frequent or recurring These symptoms should have persisted or recurred during 6 or more consecutive months of illness and they cannot have first appeared before the fatigue.

(Chronic fatigue syndrome: General information. Centers for Disease Control and Prevention. http://www.cdc.gov/cfs/general)

4. Mood Disorder/Depression

DSM-IV Criteria for Major Depressive Disorder (MDD) Diagnostic Criteria:
  i) Depressed mood or a loss of interest or pleasure in daily activities for more than two weeks.
  ii) Mood represents a change from the person's baseline.
  iii) Impaired function: social, occupational, and educational.

Specific symptoms, at least 5 of these 9, present nearly every day:
  i) Depressed mood or irritable most of the day, nearly every day, as indicated by either subjective report (e.g., feels sad or empty) or observation made by others.
  ii) Decreased interest or pleasure in most activities, most of each day.
  iii) Significant weight change (5%) or change in appetite.
  iv) Change in sleep: Insomnia or hypersomnia.
  v) Change in activity: Psychomotor agitation or retardation.
  vi) Fatigue or loss of energy.
  vii) Guilt/worthlessness: Feelings of worthlessness or excessive or inappropriate guilt.
  viii) Concentration: diminished ability to think or concentrate.
  iv) Suicidality: Thoughts of death or suicide, or has suicide plan.

Beck Depression scale used to quantify level of depression (Beck, et al. (1961) Arch Gen Psychiatry 4, 561-571).

5. Chronic (Generalized) Anxiety Disorder/Post-Traumatic Stress Disorder (PTSD)

Diagnostic Criteria:

At least 6 months of "excessive anxiety and worry" about a variety of events and situations. Generally, "excessive" can be interpreted as more than would be expected for a particular situation or event. Most people become anxious over certain things, but the intensity of the anxiety typically corresponds to the situation.

There is significant difficulty in controlling the anxiety and worry. If someone has a very difficult struggle to regain control, relax, or cope with the anxiety and worry, then this requirement is met.

The presence, for most days over the previous six months, of 3 or more (only 1 for children) of the following symptoms, which are not part of another mental disorder:
  i) Feeling wound-up, tense, or restless
  ii) Easily becoming fatigued or worn-out
  iii) Concentration problems
  iv) Irritability
  v) Significant tension in muscles
  vi) Difficulty with sleep The symptoms cause "clinically significant distress" or problems functioning in daily life. "Clinically significant" is the part that relies on the perspective of the treatment provider. Some people can have many of the aforementioned symptoms and cope with them well enough to maintain a high level of functioning.

The condition is not due to a substance or medical issue (Anxiety disorders. In: Diagnostic and Statistical Manual of Mental Disorders DSM-IV-TR. 4th ed. Arlington, Va.: American Psychiatric Association; 2000. http://www.psychiatryonline.com)

6. Chronic Headache (HA)

International Headache Society Diagnostic Criteria:

In 1988 the International Headache Society published criteria for the diagnosis of a number of different headache types. This document was updated and published in 2004 (Cephalalgia 24 (Suppl. 1), 1-151).

Tension-Type Headache Diagnostic Criteria:
  i) Headache lasting from 30 minutes to seven days.
  ii) At least two of the following criteria:
    (a) Pressing/tightening (non-pulsatile) quality
    (b) Mild or moderate intensity (may inhibit, but does not prohibit activity)
    (c) Bilateral location
    (d) No aggravation by walking, stairs or similar routine physical activity
  iii) Both of the following:
    (a) No nausea or vomiting (anorexia may occur)
    (b) Photophobia and phonophobia are absent, or one but not both are present Cervicogenic Headache Diagnostic Criteria:
  i) Pain localized to the neck and occipital region. May project to forehead, orbital region, temples, vertex or ears.
  ii) Pain is precipitated or aggravated by special neck movements or sustained postures.
  iii) At least one of the following:
    (a) Resistance to or limitation of passive neck movements.
    (b) Changes in neck muscle contour, texture, tone or response to active and passive stretching and contraction.
    (c) Abnormal tenderness of neck muscles.
  iv) Radiological examination reveals at least one of the following:
    (a) Movement abnormalities in flexion/extension
    (b) Abnormal posture
    (c) Fractures, congenital abnormalities, bone tumors, rheumatoid arthritis or other distinct pathology (not spondylosis or osteochondrosis)

7. Cognitive Dysfunction or Impairment

Cognitive dysfunction or impairment, also referred to as brain fog or mental fog, is the loss of intellectual functions (such as thinking, remembering, and reasoning) of sufficient severity to interfere with daily functioning. Patients with cognitive dysfunction have trouble with verbal recall, basic arithmetic, and concentration.

Diagnostic Criteria:

Patient improvement was quantified using the Mental Clutter Scale (Leavitt, et al. (2011) Psychological Reports 109, 445-452).

8. Interstitial Cystitis

Diagnostic Criteria:

Diagnosis of interstitial cystitis is grounded in the symptomatology of pelvic pain and urinary frequency that is of a chronic nature and unexplained by any known urologic or other system pathology (P. Hanno (2002) Rev. Urol. 4(Suppl. 1): S3-S8.

9. Chronic Pain

Chronic pain generally refers to persistent, non-acute, sometimes disabling pain in the extremities or other areas of the body. The pain can be associated with a known cause such as a major or minor injury, or it can be a symptom of a painful chronic condition such as fibromyalgia. It can just as often be of unknown origin. The term chronic pain can refer to pain that has been present for an arbitrarily defined period, for example, longer than 6 months. Alternatively, the term "chronic pain" is often used as a synonym for the term "chronic pain syndrome," a descriptive term used to indicate persistent pain, subjective symptoms in excess of objective findings, associated dysfunctional pain behaviors, and self-limitation in activities of daily living. Chronic pain syndrome (CPS) is the presentation of combined physical and psychological changes due to chronic pain.

Patients classified with chronic pain fit the 6 criteria blow:
i) Dramatization of complaints
ii) Drug misuse
iii) Dysfunction
iv) Dependency
v) Depression
vi) Disability Results:

The results, presented in the table below, are based on patients response to a visual analogue scale (VAS) for pain (Hurst, et al. (2004) J. Manip. Physiol. Therap. (JMPT) 27, 26-35). Individual values represent improvement on a scale from 1-7 as follows: 1—no change or condition has worsened; 2—Almost the same, hardly any change; 3—A little better, but the change has not made any real difference; 4—Somewhat better, but the change has not made any real difference; 5—Moderately better, and a slight but noticeable change; 6—Better, and a definite improvement that has made a real and worthwhile difference; 7—A great deal better, and a considerable improvement that has made all the difference.

Patients showing a % Pain Improvement of >30% are considered clinically responsive to the therapy.

Example B

Human Clinical Trial Protocol (PRID-201)

TITLE: A Double-Blinded, Randomized, Placebo-Controlled, Proof of Concept Phase 2a Study Exploring the Safety and Efficacy of Famciclovir+Celecoxib in the Treatment of Patients with Fibromyalgia.

OBJECTIVE: To explore the safety and efficacy of the combination of celecoxib+famciclovir vs. placebo in the treatment of fibromyalgia (FM).

Study Design:

Randomized, double-blind, placebo-controlled, 16-week study to evaluate the safety and efficacy of famciclovir and celecoxib combination for the treatment of FM patients. During the first week of treatment, a loading dose of famciclovir (2× maintenance dose) twice a day (BID) will be employed, followed by 15 weeks of maintenance dose of famciclovir BID. Depending on the patient population of the study group, use of a loading dose greater than 1000 mg/day is optional. The celecoxib dosage (also BID) will remain constant throughout the 16 weeks of active treatment.

TABLE A

Clinically - Treated Patient Responses

| Patient ID | A | B | C | D | E | F | G | H | I | J | K | L | M | N |
|---|---|---|---|---|---|---|---|---|---|---|---|---|---|---|
| 01-9221 | 84 | 7.0 | 2.0 | FM | 71.4% | 7 | | | | | 3 | | | 6 |
| 02-9218 | 94 | 10.0 | 4.0 | Brian Fog | 60.0% | 7 | 6 | 7 | | | | | 7 | |
| 03-9046 | 223 | n/a | n/a | Chronic Anxiety | n/a | | | 3 | | | | | | 3 |
| 04-9122 | 162 | 10.0 | 2.0 | FM | 80.0% | 7 | | 7 | | | 7 | 6 | | |
| 05-9284 | 43 | 5.5 | 4.0 | FM | 27.3% | 5 | | | | 4 | | | | 6 |
| 06-9013 | 239 | 8.0 | 5.0 | IBS | 37.5% | 6 | | | | 5 | | | | |
| 07-7135 | 49 | 8.0 | 2.0 | Chronic Pain | 75.0% | | 6 | | 7 | | | | 7 | |
| 08-9164 | 114 | n/a | n/a | IBS | n/a | | | 6 | | 7 | | | 6 | 7 |
| 09-8926 | 169 | 7.0 | 0.0 | CFS | 100.0% | | 7 | | 7 | 7 | | | | |
| 10-9222 | 88 | 10.0 | 5.0 | FM | 50.0% | 5 | 4 | | | | 6 | 6 | | |
| 11-9118 | 56 | 8.0 | 6.0 | Chronic Pain | 25.0% | | | 2 | 4 | | | | | |
| 12-9203 | 105 | 8.0 | 5.0 | FM | 37.5% | 6 | | | | | 5 | | 4 | 4 |
| 13-9195 | 105 | 8.0 | 7.0 | FM | 12.5% | 2 | | 1 | | | 3 | | 1 | |
| 14-9199 | 106 | 10.0 | 3.0 | IBS | 70.0% | | | | 7 | 6 | 7 | | 7 | 5 |
| 15-9243 | 70 | 10.0 | 2.0 | FM | 80.0% | 7 | 4 | | | | | | | |
| 16-9314 | 31 | 8.0 | 3.0 | CFS | 62.5% | 6 | 4 | | | | | | | |
| 17-9209 | 101 | 10.0 | 7.0 | FM | 30.0% | 4 | | 1 | | | 4 | 7 | 1 | |
| 18-9227 | 86 | 10.0 | 0.0 | FM | 100.0% | 6 | 3 | | | | 3 | | | 6 |
| 19-9312 | 30 | n/a | n/a | Brain Fog | n/a | | 2 | 3 | | | | | | |
| 20-9196 | 63 | 8.5 | 2.5 | Chronic Pain | 70.6% | | 7 | | 7 | 6 | | | 7 | |
| 21-9208 | 100 | 8.0 | 7.0 | CFS | 12.5% | 3 | 4 | | | 3 | | | | |
| 22-9252 | 87 | 9.0 | 4.0 | CFS | 55.6% | | 4 | 4 | 6 | | | | | |
| 28-8043 | 132 | 7.0 | 4.0 | FM | 42.9% | 4 | | 4 | | | 1 | 1 | 2 | 6 |
| 39-9138 | 142 | 10.0 | 7.0 | FM | 30.0% | 3 | | 1 | | | 3 | 1 | 2 | 3 |
| 41-9207 | 113 | 8.5 | 2.0 | FM | 76.5% | 5.5 | | | | | 2 | 7 | 2 | |

Legend:
A: Length of Treatment (Days),
B: Pain Initial VAS,
C: Pain Follow-Up VAS,
D: Predominant Disease,
E: Pain Improvement,
F: Fibromyalgia,
G: Cognitive Dysfunction/Brain Fog,
H: Chronic Anxiety Disorder/PTSD,
I: Chronic Pain,
J: Chronic Fatigue,
K: Chronic Headache,
L: Interstitial Cystitis,
M: Mood disorder/Depression,
N: IBS.
(n/a: not available)

Patients will be randomized to treatment with either combination therapy or placebo.

Qualified patients will have primary FM (defined by the 2010 American College of Rheumatology diagnostic criteria for FM [Wolfe, et al. (2010) Arthritis Care & Res. 62(5), 600-610], and an absence of other sources of significant pain related to systemic auto-immune diseases, structural or traumatic rheumatic conditions, or other conditions that could compromise the interpretation of study results.

Patients will undergo initial screening procedures, after which they proceed with the washout of excluded medications, if required. Patients dependent upon opioids or narcotics for pain control should not be enrolled in the study.

Due to the celecoxib component, patients will discontinue regular use of all other non-steroidal anti-inflammatory drugs (NSAIDs) at the time of randomization. Acetaminophen may be utilized throughout the study at doses not to exceed 3250 mg per day. Patients may also continue low-dose aspirin for cardioprotection (<325 mg/day), triptans and ergotamines for migraine, and dopaminergic agents for restless leg syndrome, as well as muscle relaxants, sleeping aids and benzodiazepines (assuming no evidence of abuse or dependency). Tramadol may be utilized as a rescue therapy for severe flares of FM or other acutely painful conditions (e.g., injury; procedure-related pain). Tramadol should not be taken within 48 hours of the Week 2, 6 and 12 study visits, or within 7 days of the Baseline and Week 16 visits.

Metabolic profiles of each patient's concomitant medications should be assessed to ensure there is no risk of significant drug-drug interactions with either drug. For drugs that are metabolized by CYP2C9, the concomitant use of fluconazole—a potent CYP2C9 inhibitor—should be avoided.

Patients will not be allowed to take duloxetine, milnacipran, pregabalin and sodium oxybate during the trial, and a seven day washout interval prior to randomization is required. In addition, to qualify for the study, each patient's 24 hour recall pain score must be between 40 and 90 on a 100 mm visual analog scale (VAS) at the screening visit and between 4 and 9 on a numerical rating scale (NRS) at the Baseline visit.

After ensuring that all entry criteria have been satisfied and washout successfully completed, patients will return for baseline assessments and randomization. The day of the baseline assessments will be referred to as Day 0; patients will initiate study drug either with the evening dose on Day 0 or the morning dose on the following day (Day 1), continuing with BID treatment for the duration of the study.

Blood will be collected at the screening visit for safety assessments and for exploratory cytokine analyses (e.g., IL-1β, IL-4, IL-6, IL-8, IL-10, TNF-α, IFN-α, IFN-β, IFN-γ). A second sample for cytokine analyses will also be obtained at the Baseline/randomization visit. Follow-up blood sampling for safety and cytokine analyses will take place at the Week 6 and 16 visits (or at the time of early termination). A standard urinalysis panel will be included as part of the safety labs collected at screening, Week 6 and Week 16.

Study drugs will be over-encapsulated to maintain the double-blind, and active and placebo patients will receive identical-appearing supplies of study drug. Study drug will be provided in 2-week bottles; therefore, patients will receive 1, 2, or 3 separate bottles of each drug (or matching placebo) at every study visit, depending on the number of weeks until the next scheduled visit. For the first week only, the patient will receive a third bottle which contains additional famciclovir to provide a one week loading dose.

Patients will take one capsule BID (with meals) from each of the 3 bottles assigned for the first week, followed by one capsule BID from each of the 2 bottles provided for subsequent weeks. Patients will receive study drug treatment for a total of 16 weeks, with study visits during the active treatment phase of the study scheduled for Weeks 2, 6, 12 and 16, or early termination (ET).

Inclusion Criteria:
1. Willing and able to read, understand, and sign the informed consent.
2. Male or female, 18-70 years of age, inclusive.
3. Each female patient must have a negative urine pregnancy test at Screening and Baseline unless she is post-menopausal.
4. Females of child-bearing potential must be willing to utilize an effective birth control method for the duration of their study participation.
5. Diagnosis of primary FM.
6. In the opinion of the Investigator, the patient is willing and able to comply with all protocol-specified requirements Exclusion Criteria:
1. Breastfeeding or pregnant.
2. Investigational drug usage within 30 days of Screening.
3. Diagnosed with failed back syndrome, infectious arthritis, rheumatoid arthritis, systemic lupus erythematosis, or other systemic auto-immune diseases.
4. In the opinion of the Investigator, any clinically significant, uncontrolled or unstable medical, psychiatric or surgical condition that could affect the patient's ability to participate in the study or potentially compromise his/her well-being while enrolled in the study.
5. Current systemic infection (e.g., HIV, hepatitis).
6. History of significant adverse reaction or allergy to study drugs.
7. In the opinion of the Investigator, evidence of clinically significant laboratory abnormality(ies) based on the results of the screening laboratory assessments and/or medical history.

Study Drugs:

The individual study drugs being evaluated in combination, as described herein, have been extensively studied individually in humans as well as animals. The doses and duration of treatment to be evaluated in these studies are consistent with each individual drug's current FDA-approved product labeling.

Study drug will be blinded by over-encapsulation of medications. Each medication will be provided in a separate bottle and clearly labeled in a blinded fashion. Placebo will be provided in capsules and bottles identical to those used for active study drug. All patients will take one capsule from each assigned bottle twice daily, with meals.

The Patient Groups and treatments for the study are summarized below:

Patient Treatment Groups

TABLE B

| | Famciclovir + Celecoxib | | |
|---|---|---|---|
| GROUP | DRUG | TOTAL DAILY LOADING DOSE (mg) (Week 1) | TOTAL DAILY MAINTENANCE DOSE (mg) (Weeks 2-16) |
| Placebo | Famciclovir | 0 | 0 |
| | Celecoxib | 0 | 0 |

TABLE B-continued

Famciclovir + Celecoxib

| GROUP | DRUG | TOTAL DAILY LOADING DOSE (mg) (Week 1) | TOTAL DAILY MAINTENANCE DOSE (mg) (Weeks 2-16) |
|---|---|---|---|
| A | Famciclovir | 500 | 250 |
|   | Celecoxib | 200 | 200 |
| B | Famciclovir | 500 | 250 |
|   | Celecoxib | 400 | 400 |
| C | Famciclovir | 500 | 250 |
|   | Celecoxib | 800 | 800 |
| D | Famciclovir | 1000 | 500 |
|   | Celecoxib | 200 | 200 |
| E | Famciclovir | 1000 | 500 |
|   | Celecoxib | 400 | 400 |
| F | Famciclovir | 1000 | 500 |
|   | Celecoxib | 800 | 800 |
| G | Famciclovir | 2000 | 1000 |
|   | Celecoxib | 200 | 200 |
| H | Famciclovir | 2000 | 1000 |
|   | Celecoxib | 400 | 400 |
| I | Famciclovir | 2000 | 1000 |
|   | Celecoxib | 800 | 800 |

In addition, further studies will be performed, either simultaneously or subsequent to the combination studies described above, consistent with FDA "Draft Guidance for Industry: Codevelopment of Two or More Unmarketed Investigational Drugs for Use in Combination" (December 2010). Specifically, studies will be employed to determine the contributions of the individual drugs used in combination. By way of example, a four-arm factorial study design may be used to compare results from the combination therapy to individual components and placebo (e.g., A+B v. A v. B v. placebo). These comparative studies, when done subsequent to the dose-ranging studies described herein, will utilize doses that produced the best results, while comparative studies done simultaneously may utilize multiple doses, possibly favoring the higher range of doses.

Results:
Efficacy Measures
The primary outcome measure will be the patient's self-reported 24-hour recall average pain severity, evaluated on an 11 point numerical rating scale (NRS).
Secondary measures will include:
  Patient's self-reported Global Impression of Change (PGIC)
  Revised Fibromyalgia Impact Questionnaire (FIQ-R)
Exploratory measures will include:
  Changes in cytokines associated with inflammation and/or viral infection
  NIH Patient Reported Outcomes Measurement Information System (PROMIS) fatigue questionnaire
  Multi-Dimensional Fatigue Inventory (MFI-20)
  Beck Depression Inventory (BDI-II)
Safety Measures
Safety measures include vital signs (sitting blood pressure and heart rate, oral temperature, weight), adverse events and clinical laboratory assessments.

Statistical Analyses:
The primary efficacy assessment for the determination of therapeutic efficacy will be the change from baseline in the 24-hour recall pain score as recorded on the 11-point NRS over 16 weeks of treatment. Change from baseline will be determined by comparing the baseline 24 hour recall pain score to that determined at Weeks 6, 12 and 16 /ET.

The mean change from baseline in the combination drug treatment groups will be compared to that determined for the placebo treatment group over 16 weeks of treatment using a mixed model repeated measures (MMRM). The null hypothesis will be that there is no difference between treatment groups in terms of the mean change from baseline. Rejection of this hypothesis will indicate efficacy of the combination therapy.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A fixed-dose drug combination comprising famciclovir and celecoxib in a dosage amount effective for coacting chronic disease treatment, wherein the amount of famciclovir is present in one or multiple unit dosage forms to provide a total daily dose in a range from about 500 mg to about 2000 mg, and wherein the amount of celecoxib is present in one or multiple unit dosage forms to provide a total daily dose in a range from about 300 mg to about 400 mg.

2. The fixed-dose drug combination of claim 1, wherein the famciclovir is present in a unit dosage form from about 125 mg to about 500 mg.

3. The fixed-dose drug combination of claim 1, wherein the famciclovir is present in a unit dosage form from about 500 mg to about 1000 mg.

4. The fixed-dose drug combination of claim 1, wherein the famciclovir is present in a unit dosage form selected from the group consisting of about 125 mg, about 250 mg, about 500 mg and about 1000 mg.

5. The fixed-dose drug combination of claim 1, wherein the famciclovir is present in a unit dosage form of about 250 mg or about 500 mg.

6. The fixed-dose drug combination of claim 1, wherein the celecoxib is present in a unit dosage form from about 100 mg to about 400 mg.

7. The fixed-dose drug combination of claim 1, wherein the celecoxib is present in a unit dosage form selected from the group consisting of about 100 mg, about 200 mg, and about 400 mg.

8. The fixed-dose drug combination of claim 7, wherein the celecoxib is present in a unit dosage form of about 100 mg.

9. The fixed-dose drug combination of claim 8, wherein the famciclovir is present in a unit dosage form of about 250 mg or about 500 mg.

10. The fixed-dose drug combination of claim 1, wherein the famciclovir and celecoxib are each present in an amount effective to achieve a fibromyalgia-treatment effective combination.

11. A drug-combination therapy comprising famciclovir and celecoxib in a dosage amount effective for coacting chronic disease treatment, wherein the amount of famciclovir is present in a total daily dose in a range of about 500 mg to about 2000 mg, and wherein the amount of celecoxib is present in a total daily dose in a range of about 300 mg to about 400 mg.

12. The drug-combination therapy of claim 11, wherein the famciclovir is present in a unit dosage form from about 125 mg to about 500 mg.

13. The drug-combination therapy of claim 12, wherein the celecoxib is present in a unit dosage form from about 100 mg to about 200 mg.

14. The drug-combination therapy of claim 13, wherein the famciclovir is present in a unit dosage form to provide a total daily dose in a range from about 500 mg to about 1000 mg, and wherein the celecoxib is present in a unit dosage form to provide a total daily dose of about 300 mg.

15. The drug-combination therapy of claim 14, wherein the famciclovir and celecoxib are each present in an amount effective to achieve a fibromyalgia-treatment effective combination.

* * * * *